US008377981B2

(12) United States Patent
Boger

(10) Patent No.: US 8,377,981 B2
(45) Date of Patent: Feb. 19, 2013

(54) CBI DERIVATIVES SUBJECT TO REDUCTIVE ACTIVATION

(75) Inventor: Dale Boger, LaJolla, CA (US)

(73) Assignee: The Scripps Research Institute, LaJolla, CA (US)

( * ) Notice: Subject to any disclaimer, the term of this patent is extended or adjusted under 35 U.S.C. 154(b) by 190 days.

(21) Appl. No.: 12/742,616

(22) PCT Filed: Nov. 13, 2008

(86) PCT No.: PCT/US2008/083433
§ 371 (c)(1),
(2), (4) Date: May 12, 2010

(87) PCT Pub. No.: WO2009/064908
PCT Pub. Date: May 22, 2009

(65) Prior Publication Data
US 2011/0112163 A1    May 12, 2011

Related U.S. Application Data

(60) Provisional application No. 61/002,978, filed on Nov. 13, 2007, provisional application No. 60/987,647, filed on Nov. 13, 2007.

(51) Int. Cl.
*A61K 31/403* (2006.01)
*C07D 403/14* (2006.01)
*C07D 403/06* (2006.01)
*A61P 35/00* (2006.01)

(52) U.S. Cl. ........ 514/411; 548/427; 548/455; 514/414; 514/375; 514/410

(58) Field of Classification Search .................. None
See application file for complete search history.

(56) References Cited

U.S. PATENT DOCUMENTS

| 6,756,397 B2 * | 6/2004 | Zhao et al. ............ 514/411 |
| 2004/0002528 A1 * | 1/2004 | Boger ............ 514/375 |
| 2005/0026987 A1 | 2/2005 | Boger |
| 2005/0032860 A1 | 2/2005 | Boger |

OTHER PUBLICATIONS

WO 2009/064908 First page and International Search Report.
Lajiness et al., *J. Med. Chem.* 2010 53:7731-7738.
Jin et al., *J. Am. Chem. Soc.* 2007 129:15391-15397.

* cited by examiner

*Primary Examiner* — Dennis Heyer
(74) *Attorney, Agent, or Firm* — Husch Blackwell LLP

(57) ABSTRACT

A unique class of N-acyl O-amino phenol prodrugs of CBI-TMI and CBI-indole$_2$ were synthesized and shown to be prodrugs, subject to reductive activation by nucleophilic cleavage of a weak N—O bond, effectively releasing the free drug in functional cellular assays for cytotoxic activity approaching or matching the activity of the free drug, yet remain essentially stable to ex vivo DNA alkylation conditions. Most impressively, assessment of the in vivo antitumor activity of a representative O-(acylamino) prodrug, 8, indicate that they approach the potency and exceed the efficacy of the free drug itself (CBI-indole$_2$), indicating that the inactive prodrugs not only effectively release the free drug in vivo, but that they offer additional advantages related to a controlled or targeted release in vivo.

8 Claims, 1 Drawing Sheet

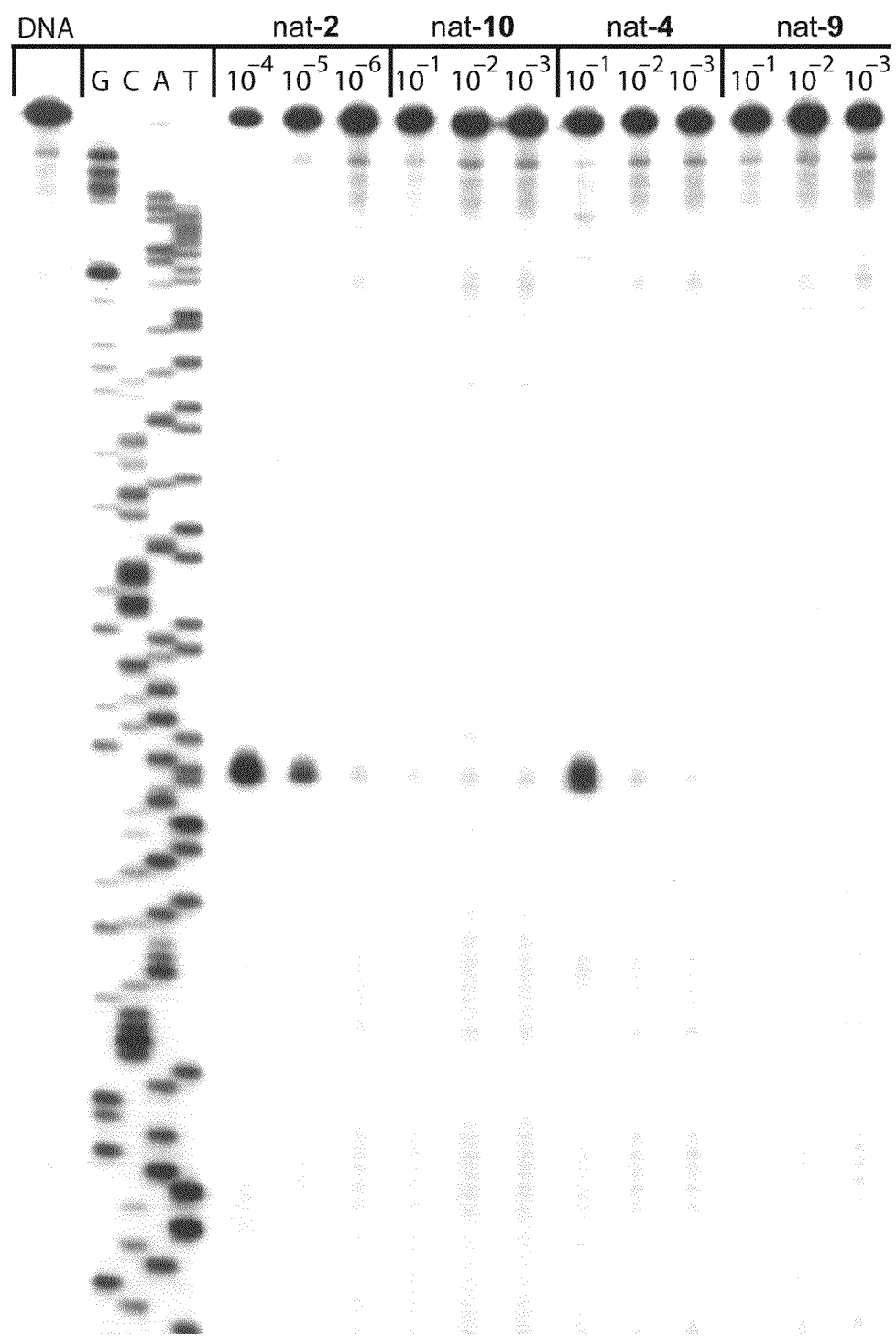

CBI DERIVATIVES SUBJECT TO REDUCTIVE ACTIVATION

CROSS-REFERENCE TO RELATED APPLICATION

This application claims priority of provisional application Ser. No. 61/002,978 and Ser. No. 60/987,647, both of which were filed on Nov. 13, 2007, and whose disclosures are incorporated by reference.

GOVERNMENTAL SUPPORT

The present invention was made with governmental support under Contract No. CA041986 awarded by the National Institutes of Health. The government has certain rights in the invention.

FIELD OF INVENTION

The invention relates to prodrug anticancer agents and to their use. More particularly, the invention relates to N-acyl O-amino phenol prodrugs of CBI-TMI and CBI-indole$_2$.

BACKGROUND

CC-1065, the duocarmycins, and yatakemycin constitute exceptionally potent naturally occurring antitumor agents that derive their biological properties through a characteristic sequence-selective DNA alkylation reaction (below) (Chidester, C. G.; et al. *J. Am. Chem. Soc.* 1981, 103, 7629; Trzupek, J. D.; et al. *Nature Chem. Biol.* 2006, 2, 79).

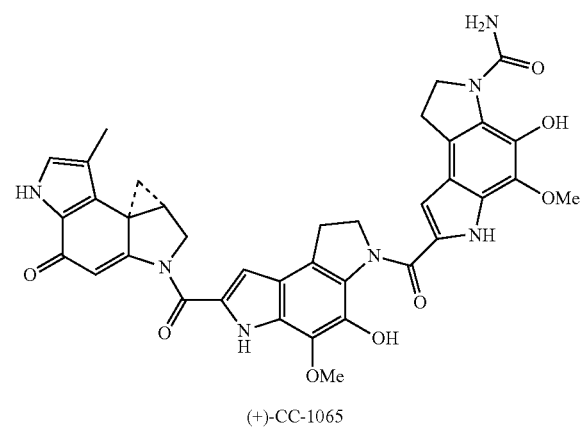

(+)-CC-1065

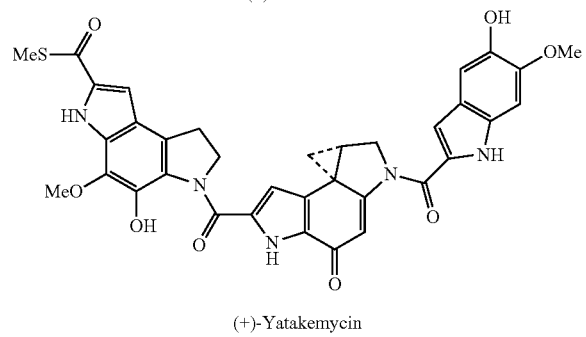

(+)-Yatakemycin

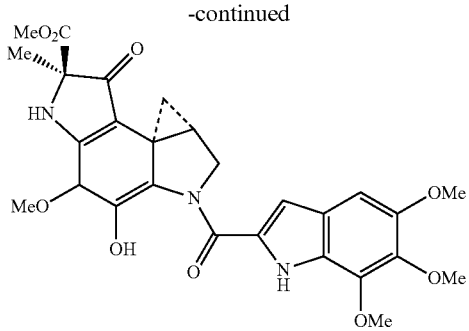

(+)-Duocarmycin A

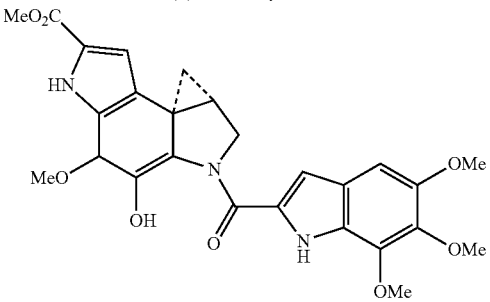

(+)-Duocarmycin SA

The examination of the natural products, their synthetic unnatural enantiomers, their derivatives, and synthetic analogues have defined fundamental features that control the alkylation selectivity, impact the alkylation efficiency, and are responsible for DNA alkylation catalysis providing a detailed understanding of the relationships between structure, reactivity, and biological activity (Warpehoski, M. A.; Hurley, L. H. *Chem. Res. Toxicol.* 1988, 1, 315; Boger, D. L. *Chem. Biol.* 2004, 11, 1607.).

One of the most important and widely explored class of analogues is CBI (Boger, D. L.; et al. *J. Am. Chem. Soc.* 1989, 111, 6461; Boger, D. L.; et al. *J. Org. Chem.* 1990, 55, 5823) (1,2,9,9a-tetrahydrocyclopropa[c]benz[e]indol-4-one), being synthetically (Boger, D. L.; et al. *J. Am. Chem. Soc.* 1989, 111, 6461; Boger, D. L.; et al. *J. Org. Chem.* 1990, 55, 5823; Boger, D. L.; et al. *J. Org. Chem.* 1992, 57, 2873; Boger, D. L.; McKie, J. A. *J. Org. Chem.* 1995, 60, 1271; Drost, K. J.; Cava, M. P. *J. Org. Chem.* 1991, 56, 2240; Aristoff, P. A.; Johnson, P. D. *J. Org. Chem.* 1992, 57, 6234; Mohamadi, F.; et al. *J. Med. Chem.* 1994, 37, 232; Ling, L.; et al. *Heterocyclic Commun.* 1997, 3, 405; Boger, D. L.; et al. *Synlett* 1997, 515; Boger, D. L.; et al. *Tetrahedron Lett.* 1998, 39, 2227; Kastrinsky, D. B.; Boger, D. L. *J. Org. Chem.* 2004, 69, 2284) more accessible than the natural products, yet indistinguishable in their DNA alkylation selectivity (FIG. 2) (Boger, D. L.; Munk, S. A. *J. Am. Chem. Soc.* 1992, 114, 5487).

Moreover, the CBI derivatives proved to be four times more stable and, correspondingly, four times more potent than derivatives bearing the CC-1065 alkylation subunit (7-MeCPI) approaching the stability and potency of duocarmycin SA and yatakemycin derivatives, and they exhibit efficacious in vivo antitumor activity in animal models at doses that reflect this potency (Boger, D. L.; et al. *Bioorg. Med. Chem. Lett.* 1991, 1, 115; Boger, D. L.; et al. *Bioorg. Med. Chem.* 1995, 3, 1429). Consequently, CBI and its derivatives have been the focus of much development as well as the prototype analogues on which new design concepts have been explored, developed, or introduced (Boger, D. L.; et al. *J. Am.*

Chem. Soc. 1989, 111, 6461; Tietze, L. F.; et al. Angew. Chem. Int. Ed. 2006, 45, 6574; Wang, Y.; et al. Bioorg. Med. Chem. 2003, 11, 1569; Jeffrey, S. C.; et al. J. Med. Chem. 2005, 48, 1344; Kline, T.; et al. Mol. Pharmaceut. 2004, 1, 9; Hay, M. P.; et al. J. Med. Chem. 2003, 46, 5533; Tercel, M.; et al. J. Med. Chem. 2003, 46, 2132; Gieseg, M. A.; et al. Anti-Cancer Drug Design 1999, 14, 77; Hay, M. P.; et al. Bioorg. Med. Chem. Lett. 1999, 9, 2237; Atwell, G. J.; et al. J. Med. Chem. 1999, 42, 3400; Atwell, G. J.; et al. J. Org. Chem. 1998, 63, 9414; Atwell, G. J.; et al. Bioorg. Med. Chem. Lett. 1997, 7, 1493; Townes, H.; et al. Med. Chem. Res. 2002, 11, 248; Boger, D. L.; Garbaccio, R. M. J. Org. Chem. 1999, 69, 8350).

A unique feature of this class of molecules including the natural products themselves is the observation that synthetic phenol precursors (e.g., 1) to the final products, entailing a Winstein Ar-3' spirocyclization with displacement of an appropriate leaving group, exhibit biological properties typically indistinguishable from the cyclopropane-containing final products (DNA alkylation rate or efficiency, in vitro cytotoxic activity, and in vivo antitumor activity). This dependable behavior of the precursor phenols has provided the basis on which the development of useful, stable, or safe prodrugs has been conducted (Carzelesin: Aristoff, P. A. Adv. Med. Chem. 1993, 2, 67. KW-2189: Kobayashi, E.; et al. Cancer Res. 1994, 54, 2404; Amishiro, N.; et al. Bioorg. Med. Chem. 2000, 8, 1637; Amishiro, N.; et al. J. Med. Chem. 1999, 42, 669; Nagamura, S.; et al. Chem. Pharm. Bull. 1996, 44, 1723; Nagamura, S.; et al. Chem. Pharm. Bull. 1995, 43. CBI: Boger, D. L.; et al. Synthesis 1999, 1505).

One feature limiting the attractiveness of this class of cytotoxic agents is their remarkable potencies ($IC_{50}$ 5-20 pM) creating special requirements for their preparation and handling. In many instances, this has been addressed by the introduction of chemically stable phenol protecting groups that are readily cleaved at the final stage of their preparation or upon in vivo administration. Such protected phenol precursors are intrinsically much less potent, yet readily release an active precursor to the drug upon deprotection. Extensions of this protection and release strategy have been pursued in which the free phenol release in vivo is coupled to features that might facilitate tumor selective delivery or cleavage (Wolkenberg, S. E.; Boger, D. L. Chem. Rev. 2002, 102, 2477. Reviews on reductive activation: Papadopoulou, M. V.; Bloomer, W. D. Drugs Future 2004, 29, 807; Jaffar, M.; Stratford, I. J. Exp. Opin. Ther. Patents 1999, 9, 1371; Patterson, L. H.; Raleigh, S. M. Biomed. Health Res. 1998, 25, 72). Such inactive prodrugs serve the dual role of providing safer handling intermediates or final products as well as potentially enhancing the therapeutic index of the drug.

As attractive and amenable as this approach is for this class of drugs, a surprisingly small series of such studies have been disclosed (Chari, R. V. J.; et al. Cancer Res. 1995, 55, 4079; Lillo, A. M.; et al. Chem. Biol. 2004, 11, 897; Tietze, L. F.; et al. Eur. J. Org. Chem. 2002, 10, 1634; Tietze, L. F.; et al. Angew. Chem. Int. Ed. 2002, 41, 759; Tietze, L. F.; et al. ChemBioChem 2001, 2, 758; Tietze, L. F.; et al. Angew. Chem. Int. Ed. 2006, 45, 6574; Wang, Y.; et al. Bioorg. Med. Chem. 2003, 11, 1569; Jeffrey, S. C.; et al. J. Med. Chem. 2005, 48, 1344; Kline, T.; et al. Mol. Pharmaceut. 2004, 1, 9; Hay, M. P.; et al. J. Med. Chem. 2003, 46, 5533; Tercel, M.; et al. J. Med. Chem. 2003, 46, 2132; Gieseg, M. A.; et al. Anti-Cancer Drug Design 1999, 14, 77; Hay, M. P.; et al. Bioorg. Med. Chem. Lett. 1999, 9, 2237; Atwell, G. J.; et al. J. Med. Chem. 1999, 42, 3400; Atwell, G. J.; et al. J. Org. Chem. 1998, 63, 9414; Atwell, G. J.; et al. Bioorg. Med. Chem. Lett. 1997, 7, 1493; Townes, H.; et al. Med. Chem. Res. 2002, 11, 248; Boger, D. L.; Garbaccio, R. M. J. Org. Chem. 1999, 69, 8350).

BRIEF SUMMARY OF THE INVENTION

N-Acyl O-amino phenol derivatives of CBI-TMI and CBI-indole$_2$ are disclosed herein as prototypical members of a new class of reductively activated prodrugs of the duocarmycin and CC-1065 class of antitumor agents. The expectation being that hypoxic tumor environments, with their higher reducing capacity, carry an intrinsic higher concentration of "reducing" nucleophiles (e.g., thiols) capable of activating such derivatives (tunable N—O bond cleavage) increasing their sensitivity to the prodrug treatment. Preliminary studies indicate the prodrugs effectively release the free drug in functional cellular assays for cytotoxic activity approaching or matching the activity of the free drug, yet remain essentially stable and unreactive to in vitro DNA alkylation conditions (<0.1-0.01% free drug release), pH 7.0 phosphate buffer, and exhibit a robust half-life in human plasma ($t_{1/2}$=3 hours). Characterization of a representative O-(acylamino) prodrug in vivo indicates that they approach the potency and exceed the efficacy of the free drug itself (CBI-indole$_2$) indicating that not only is the free drug effectively released from the inactive prodrug, but that they offer additional advantages related to a controlled or targeted release in vivo.

A contemplated compound of the invention is an N-acyl O-amino CBI derivative that is represented by Formula I:

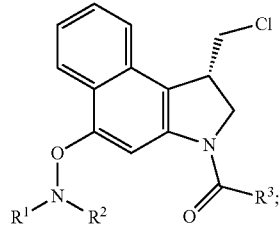

Formula I

In Formula I, $R^1$ is selected from the group of radicals consisting of —C(O)(C$_1$-C$_6$ alkyl), —C(O)O(C$_1$-C$_{10}$ alkyl), —C(O)(C$_2$-C$_6$ alkenyl), —C(O)O(C$_2$-C$_6$ alkenyl), and —C(O)aryl. $R^2$ is selected from the group of radicals consisting of hydrogen, —C(O)(C$_1$-C$_6$ alkyl), —C(O)O(C$_1$-C$_{10}$ alkyl), —C(O)(C$_2$-C$_6$ alkenyl), and —C(O)O(C$_2$-C$_6$ alkenyl). In the alternative, $R^1$ and $R^2$ are combined to form a cyclic structure selected from the group consisting of divalent radicals represented as follows:

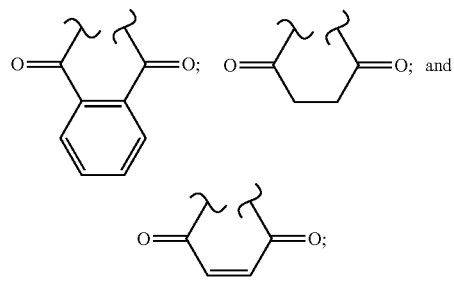

$R^3$ in Formula I is selected from group consisting of radicals represented as follows:

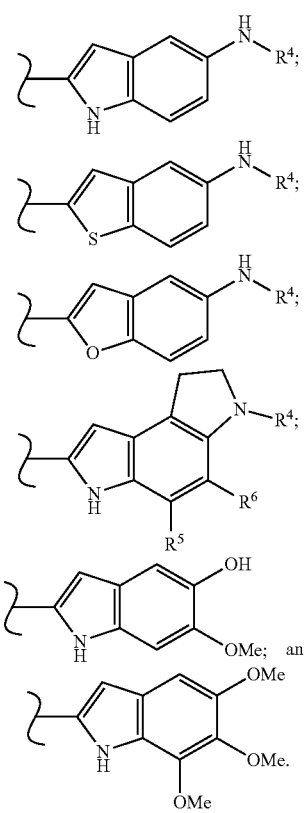

wherein R⁴ is selected from group consisting of radicals represented as follows:

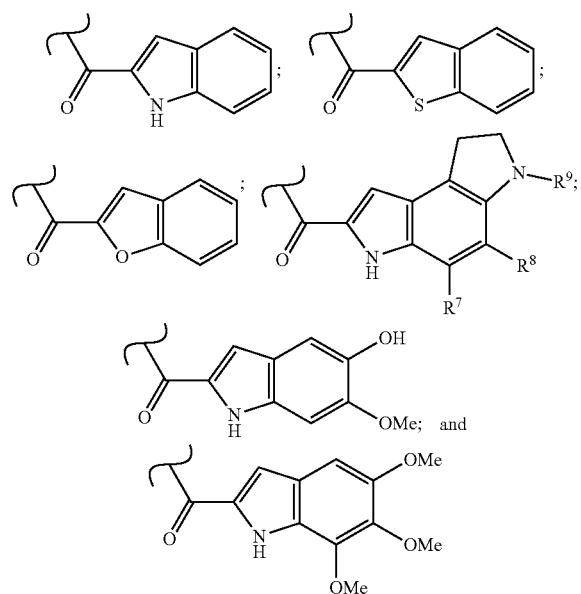

R⁵, R⁶, R⁷ and R⁸ in the above structural formulas are each independently selected from the group of radicals consisting of —H, —OH, —O($C_1$-$C_6$ alkyl), —($C_1$-$C_6$ alkyl) and halogen. R⁹ of an above formula is selected from the group of radicals consisting of —H, —C(O)O($C_1$-$C_6$ alkyl), —C(O)($C_1$-$C_6$ alkyl), —C(O)NH₂, —C(O)NHNH₂, and —C(O)NHNHC(O)O($C_1$-$C_6$ alkyl).

In a preferred compound, R⁴ is selected from the group of radicals consisting of —C(O)($C_1$-$C_6$ alkyl) and —C(O)O($C_1$-$C_{10}$ alkyl); R² is selected from the group of radicals consisting of hydrogen (hydrido; —H), —C(O)($C_1$-$C_6$ alkyl), and —C(O)O($C_1$-$C_{10}$ alkyl); or, alternatively, R⁴ and R² combine to form a cyclic divalent radical represented by the following structure (phthalyl):

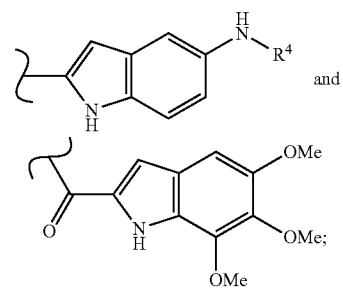

R³ is selected from the group consisting of the following radicals:

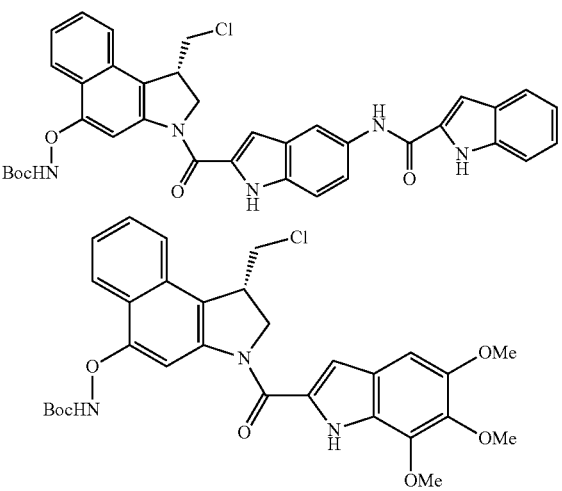

wherein:
R⁴ is

Particularly preferred compounds include those with the following structural formulas:

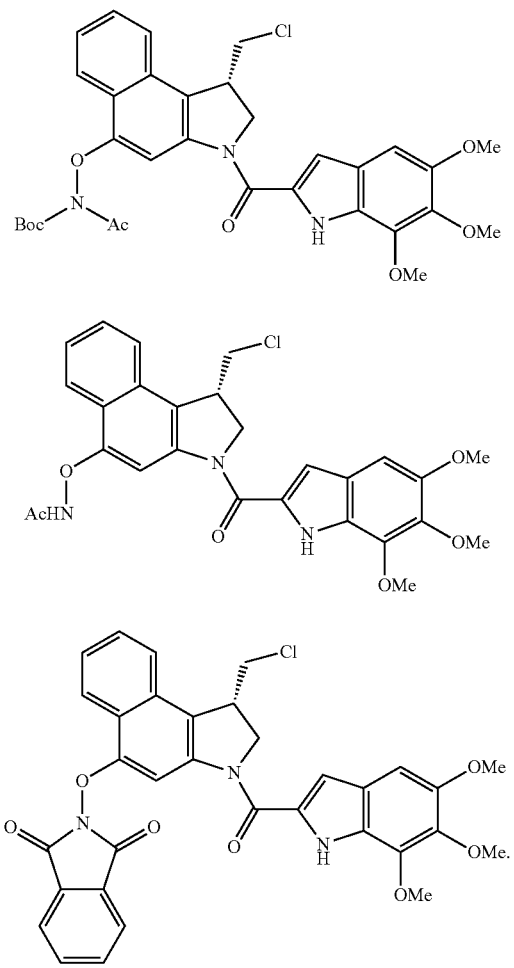

A process for treating a proliferative disease such as a cancer or leukemia in a mammal is also contemplated. In accordance with that process, an effective amount of a compound of Formula I such as one of the five compounds shown immediately above is administered to a mammal in need thereof. In yet another aspect, the use of a compound of Formula I in the manufacture of a medicament for treating a proliferative disease such as cancer or leukemia is contemplated.

It is noted that in the structural formulas utilized herein that a wavy line indicates a chemical bond to a depicted atom. It is also noted that to improve readability and minimize seeming duplication, any combination of structural elements described broadly can be present in a specific embodiment unless otherwise stated.

BRIEF DESCRIPTION OF DRAWINGS

In the drawings forming a portion of this disclosure,

FIG. 1 illustrates the results of an electrophoresis gel with 8% denaturing PAGE and autoradiography. Thermally-induced strand cleavage of w794 DNA; DNA-agent incubation at 4° C. for 18 hours, removal of unbound agent by EtOH precipitation, and 30 minutes of thermolysis (100° C.) followed by 8% denaturing PAGE and autoradiography. Lane 1, control DNA; lanes 2-5, Sanger G, C, A, and T sequencing reactions; lanes 6-8, 2 ($1\times10^{-4}$ to $1\times10^{-6}$); lanes 9-11, 10 ($1\times10^{-1}$ to $1\times10^{-3}$); lanes 12-14, 4 ($1\times10^{-1}$ to $1\times10^{-3}$), lanes 15-17, 9 ($1\times10^{-1}$ to $1\times10^{-3}$). All compounds possess the natural 1S-configuration. The reductively activated agent 4 was found to alkylate w794 DNA with an identical sequence selectivity as the parent agent CBI-TMI (2), albeit with a substantially reduced efficiency (1,000-10,000-fold). Similarly, the O-methyl ether 10 as well as 9 lacking a C4 substituent failed to exhibit significant observable DNA alkylation.

DETAILED DESCRIPTION OF THE INVENTION

A novel set of reductively activated phenol prodrugs of the CC-1065 and duocarmycin class of compounds is disclosed. These compounds do not require enzymatic release and are illustrative of other phenolic drugs that can benefit from such a designed activation. Alternative and prior efforts at incorporating a reductive activation into the CC-1065 and duocarmycin class includes the Denny disclosures of nitro precursors to aryl amine variants of the phenol precursors (Hay, M. P.; et al. *J. Med. Chem.* 2003, 46, 5533; Tercel, M.; et al. *J. Med. Chem.* 2003, 46, 2132; Gieseg, M. A.; et al. *Anti-Cancer Drug Design* 1999, 14, 77; Hay, M. P.; et al. *Bioorg. Med. Chem. Lett.* 1999, 9, 2237; Atwell, G. J.; et al. *J. Med. Chem.* 1999, 42, 3400; Atwell, G. J.; et al. *J. Org. Chem.* 1998, 63, 9414; Atwell, G. J.; et al. *Bioorg. Med. Chem. Lett.* 1997, 7, 1493), Lee's use of an ester subject to cleavage upon a tethered quinone reduction (Townes, H.; et al. *Med. Chem. Res.* 2002, 11, 248), and a report of mitomycin-like quinone precursors to a reductively activated o-spirocyclization (versus p-spirocyclization) analogous to those observed with the duocarmycins or its analogues (Boger, D. L.; Garbaccio, R. M. *J. Org. Chem.* 1999, 69, 8350).

Although the approaches have provided some increase in selectivity resulting from reductive activation, none approach that observed with mitomycin and none effectively or clearly utilize an intrinsic enzyme activity that differentiated normal versus tumor cells. Notably, it may be the ease of the mitomycin hydroquinone reoxidation to the quinone in normal cells that protects them from the effects of the drug, which occurs less readily in hypoxic tumors.

The structure of CBI (1,2,9,9a-tetrahydrocyclopropa[c]benz[e]indol-4-one) and its precursor 1 where R is just the DNA binding portion of the molecule along with its precursor, the O-amino phenol derivative or prodrug that requires reductive activation by N—O bond cleavage are shown below. The CBI compounds are more accessible than the natural products, yet indistinguishable in their DNA alkylation selectivity (Boger, D. L.; Munk, S. A. *J. Am. Chem. Soc.* 1992, 114, 5487). Moreover, the CBI derivatives proved to be four times more stable and, correspondingly, four times more potent than derivatives bearing the CC-1065 alkylation subunit (7-MeCPI) approaching the stability and potency of duocarmycin SA and yatakemycin derivatives, and they exhibit efficacious in vivo antitumor activity in animal models at doses that reflect this potency. Consequently, CBI and its derivatives have been the focus of much development as well as the prototype analogues on which new design concepts have been explored, developed, or introduced, including the instant invention.

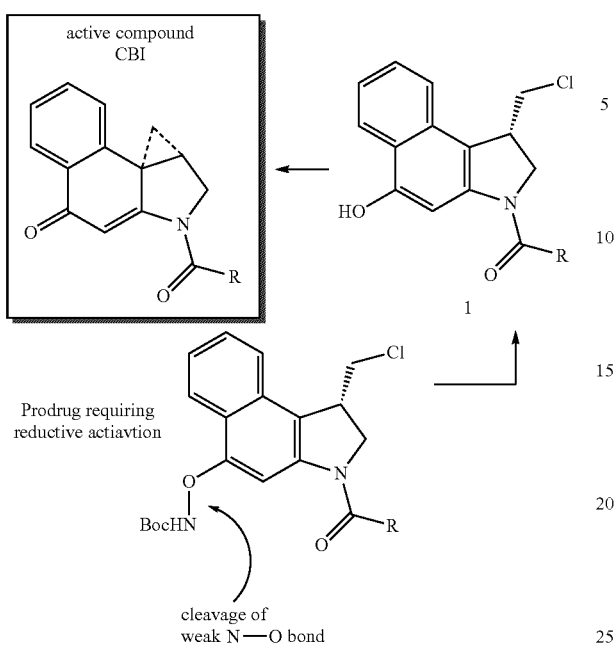

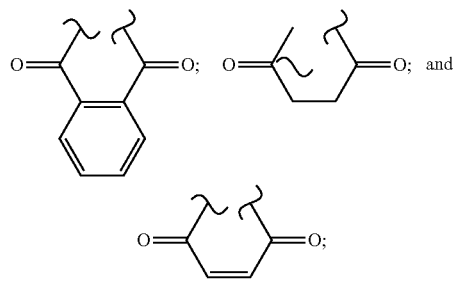

The approach detailed herein was not designed for enzymatic reductive activation, but rather for activation by cleavage of a weak N—O bond by reducing nucleophiles. The expectation of this approach being that hypoxic tumor cells, with their higher reducing capacity, contain an intrinsically higher concentration of "reducing" nucleophiles (i.e., thiols) capable of activating such derivatives making them more sensitive to the prodrug treatment (Wolkenberg, S. E.; Boger, D. L. *Chem. Rev.* 2002, 102, 2477. Reviews on reductive activation: Papadopoulou, M. V.; Bloomer, W. D. *Drugs Future* 2004, 29, 807; Jaffar, M.; Stratford, I. J. *Exp. Opin. Ther. Patents* 1999, 9, 1371; Patterson, L. H.; Raleigh, S. M. *Biomed. Health Res.* 1998, 25, 72). Moreover, as detailed below, the design lends itself to a rational tuning of the ease of reduction of the derivative allowing empirical experience with the series to guide future design.

A contemplated compound of the invention is an N-acyl O-amino CBI derivative that is represented by Formula I:

Formula I

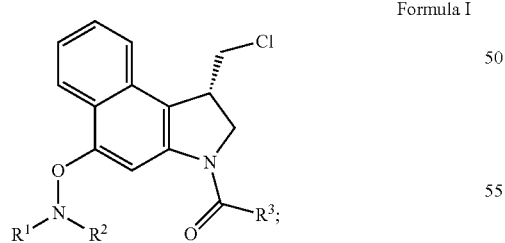

In Formula I, $R^4$ is selected from the group of radicals consisting of —C(O)($C_1$-$C_6$ alkyl), —C(O)O($C_1$-$C_{10}$ alkyl), —C(O)($C_2$-$C_6$ alkenyl), —C(O)O($C_2$-$C_6$ alkenyl), and —C(O)aryl. $R^2$ is selected from the group of radicals consisting of hydrogen, —C(O)($C_1$-$C_6$ alkyl), —C(O)O($C_1$-$C_{10}$ alkyl), —C(O)($C_2$-$C_6$ alkenyl), and —C(O)O($C_2$-$C_6$ alkenyl). In the alternative, $R^4$ and $R^2$ are combined to form a cyclic structure selected from the group consisting of divalent radicals represented as follows:

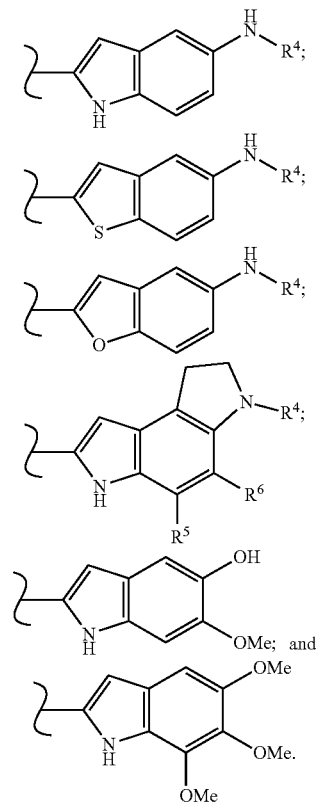

$R^3$ in Formula I is selected from group consisting of radicals represented as follows:

wherein $R^4$ is selected from group consisting of radicals represented as follows:

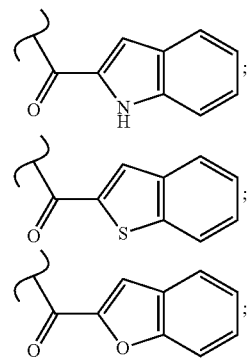

-continued

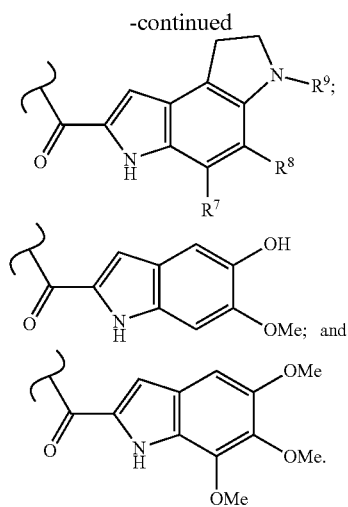

R⁵, R⁶, R⁷ and R⁸ in the above structural formulas are each independently selected from the group of radicals consisting of —H, —OH, —O(C₁-C₆ alkyl), —(C₁-C₆ alkyl) and halogen. R⁹ of an above formula is selected from the group of radicals consisting of —H, —C(O)O(C₁-C₆ alkyl), —C(O)(C₁-C₆ alkyl), —C(O)NH₂, —C(O)NHNH₂, and —C(O)NHNHC(O)O(C₁-C₆ alkyl).

In any of the Formulas herein, the term "C₁-C₆ alkyl" denotes a straight or branched chain radical such as a methyl, ethyl, n-propyl, isopropyl, n-butyl, sec-butyl, tert-butyl, amyl, tert-amyl, hexyl group and the like.

The term "C₂-C₆ alkenyl" denotes a radical such as a vinyl, allyl, 2-butenyl, 3-butenyl, 2-pentenyl, 3-pentenyl, 4-pentenyl, 2-hexenyl, 3-hexenyl, 4-hexenyl, 5-hexenyl group and the like, as well as dienes and trienes of straight and branched chains containing up to six carbon atoms and at least one carbon-to-carbon (ethylenic) double bond.

The term "halogen" includes fluoro, chloro, bromo and iodo, with chloro being preferred.

The term "aryl" is meant to include a monocyclic or dicyclic aromatic radical containing 5 to 10 atoms in the ring system and zero, one or three atoms other than carbon in the rings. The atoms other than carbon can be selected from oxygen, nitrogen and sulfur. Illustrative aryl radicals include phenyl, 1- and 2-naphthyl, pyridyl, pyrazinyl, pyrimidyl, imidazyl, thiophenyl, furanyl, pyrrolyl, 1,3,5-triaziyl, 1,2,4-triazinyl and 1,2,3-triazinyl, quinazolinyl, quinolinyl, their various positional isomers, and the like.

Pharmaceutical Compositions and Treatment Methods

A Pharmaceutical Composition for Treating

A process for treating a proliferative disease such as a cancer or leukemia in a mammal is also contemplated. Such a composition contains a pharmaceutically effective amount of a before-discussed molecule of Formula I dissolved or dispersed in a pharmaceutically acceptable diluent.

A contemplated compound of Formula I can be used in a pharmaceutical composition to treat and preferably kill cancer cells or cells of another proliferative disease such as leukemia in vitro or in vivo in a mammalian subject. Thus, an above composition is contacted with the cells to be treated. The cells so treated are maintained in contact with a compound of Formula I until cleared by the body when in vivo, or for various times as desired in an in vitro study. The treatment is generally repeated several times.

A mammal to which or whom a compound of Formula I composition is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like in need of treatment for a cancerous condition.

A contemplated composition is administered to a mammal in need of the medication at an proliferative effective dosage level. That level is typically an amount sufficient to provide about 10 to about 100 μg/kg of body weight to the recipient's plasma or serum, using the molecular weight of the scission-activated duocarmycin-type prodrug Compound 8 itself as the basis for calculation in view of the

8

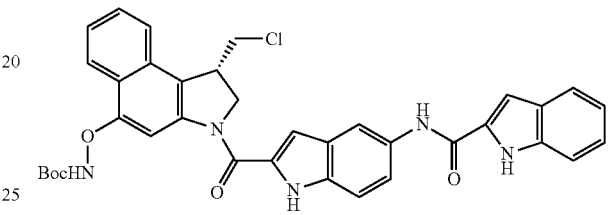

different molecular weights of the other prodrug compounds contemplated herein. The amount can vary depending on the recipient and proliferative cell load. Those plasma or serum concentrations can usually be obtained by i.v. administration using a liquid dosage form that contains about 200 mg to about 1000 mg of chimer compound per day. The determination of optimum dosages for a particular situation is within the skill of the art.

A compound of Formula I composition is administered repeatedly, on a schedule adapted for a recipient's cancer load and need, as is well known in the art. Typical administrations are given multiple times within a one month time period, usually followed by a rest period and then further administrations and rest periods until the recipient is free of the disease, or longer for prophylactic purposes.

For preparing pharmaceutical compositions containing a chimer compound of the invention, an inert, pharmaceutically acceptable carrier or diluent is used. The diluent is usually in liquid form.

Liquid pharmaceutical compositions include, for example, solutions suitable for parenteral administration. Sterile water solutions of the active chimer or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, in vials or ampules.

Chemistry

Synthesis

A range of methods for direct conversion of a precursor phenol to the corresponding O-amino phenol were examined (O-amidation) and several routes to the final compounds were explored. It was anticipated that this might best be conducted on a seco-N-Boc-CBI derivative lacking the capabilities of spirocyclization (e.g., 11). However, the lability of the resulting N-acyl O-amino phenol derivatives to subsequent chemical transformations proved significant and this approach proved less viable than a surprisingly effective direct O-amidation reaction of seco-CBI-TMI or seco-CBI-indole$_2$.

Schemes 1A and 1B, below, show the synthesis of the N-acyl O-amino phenols directly from the precursors 2 and 3. Thus, low temperature phenol deprotonation of 2 (3 equiv of LiHMDS, 0° C., ether-dioxane) followed by treatment with the amidating reagents TsONHBoc (Greck, C.; et al. *Bull. Soc. Chim. Fr.* 1994, 131, 429) or TsONPhth (Neumann, U.; Gütschow, M. *J. Biol. Chem.* 1994, 269, 21561) provided 4 and 8 directly in good conversions. Competitive spirocyclization of 2 to CBI-TMI itself was observed if the deprotonation was carried out at higher reaction temperatures or in more polar solvents. It diminished as the solvent polarity was reduced (glyme>THF>dioxane-ether>ether, insoluble) and was less prominent with LiHMDS versus NaHMDS.

In most instances, recovered starting phenol was present in the crude reaction product and was chromatographically close enough to the N-acyl O-amino phenols that special precautions were taken to ensure its removal. This entailed exposure of the product mixture to conditions that promote deliberate spirocyclization of the seco phenol derivatives [saturated aqueous NaHCO$_3$-THF (1:1), 23° C., 2 hours (h)] and subsequent chromatographic separation of the much more polar CBI-TMI or CBI-indole$_2$. N-Acetylation of 4 (Ac$_2$O, cat. DMAP, CH$_2$Cl$_2$, 23° C., 12 h, 81%) provided 6 and subsequent Boc deprotection (TFA-CH$_2$Cl$_2$ (1:1), 23° C., 3 hours, 88%) afforded 5. In an analogous manner, seco-CBI-indole$_2$ (3) was directly converted to 8 (45%) upon LiHMDS deprotonation (3 equiv of LiHMDS, ether-dioxane, 0° C., 30 minutes) and subsequent O-amidation with TsONHBoc (Greck, C.; et al. *Bull. Soc. Chim. Fr.* 1994, 131, 429).

Scheme 1A

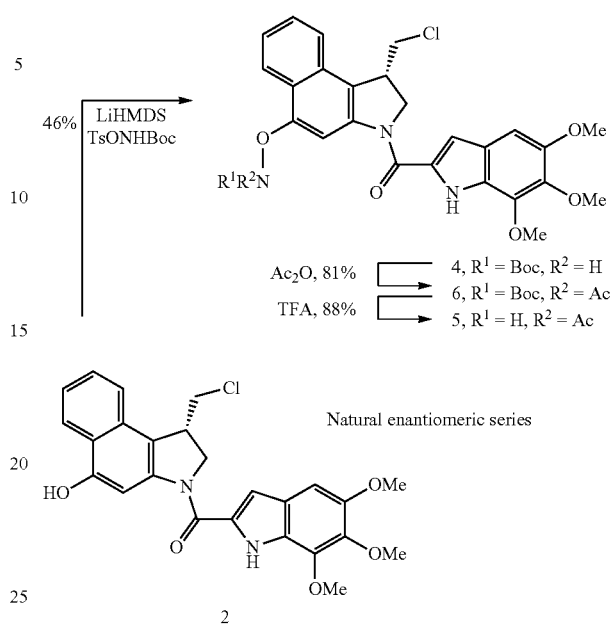

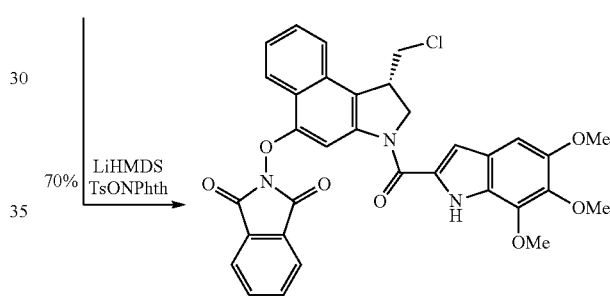

Scheme 1B

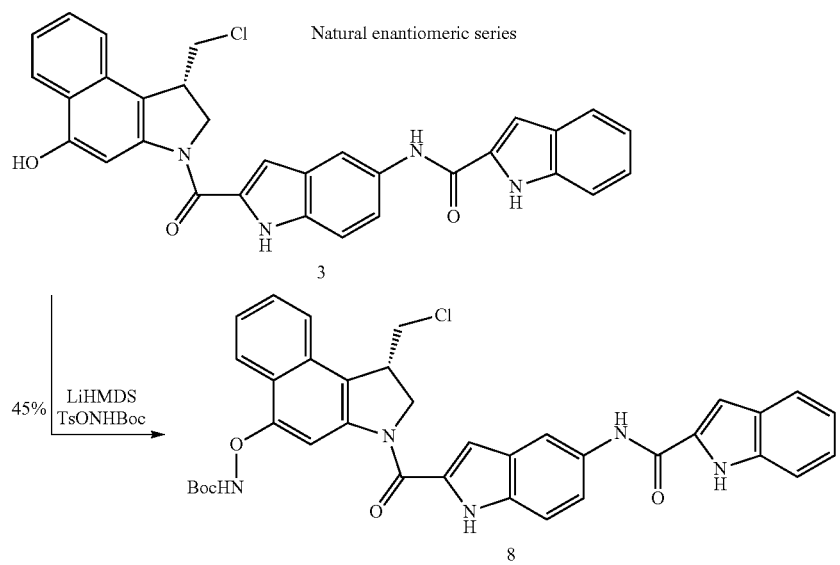

For comparison purposes, two analogues of seco-CBI-TMI were prepared that are incapable of spirocyclization to CBI-TMI itself. The first incorporates the C4 phenol protected as its methyl ether (10) and second contains no C4 substituent (9). The former was prepared from 11 (Kastrinsky, D. B.; Boger, D. L. *J. Org. Chem.* 2004, 69, 2284) by phenol O-methylation, primary alcohol OTBS deprotection and subsequent conversion to the primary chloride 14, followed by N-Boc deprotection and coupling with 5,6,7-trimethoxyindole-2-carboxylic acid (15) to provide 10. See, Scheme 2, below.

Scheme 2

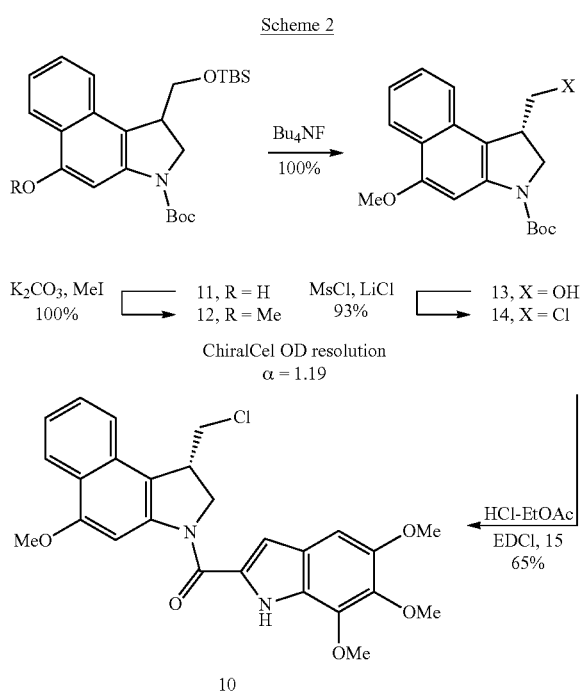

Scheme 3

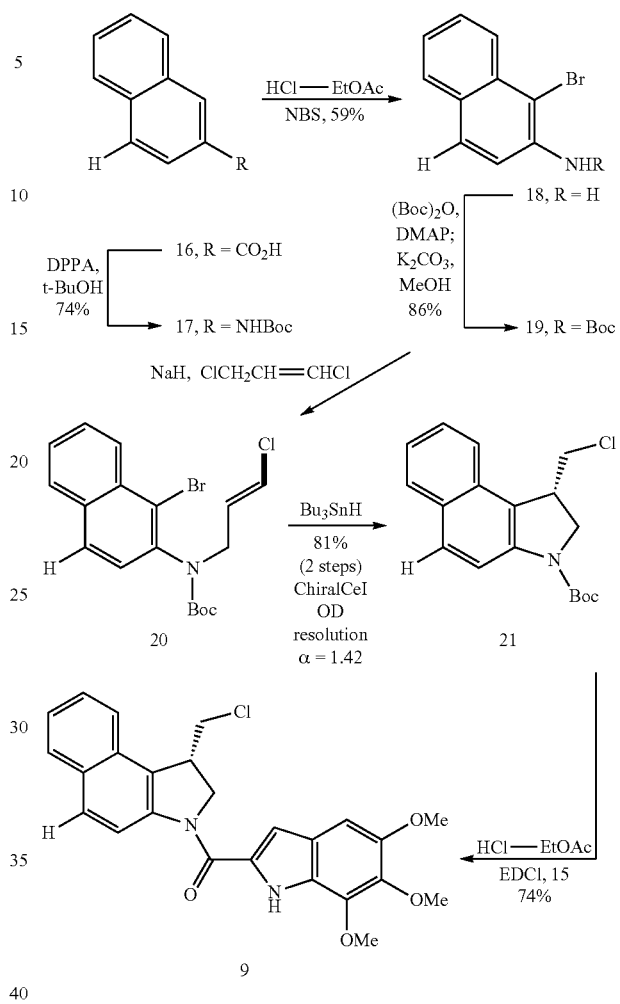

Throughout this sequence and as a result of the multiple purifications, the chances of residual, contaminant phenol (2) being present in the final product 10 are remote. Nonetheless, because even trace quantities of 2 can be misleadingly detected in the subsequent biological evaluations (e.g., 0.01%), the inactive analogue 9 was also prepared for comparison and by an approach that precludes the presence of such a contaminate phenol because there is no C-4 functionality in the starting material 16.

Thus, following a route analogous to that used for CBI itself (Boger, D. L.; et al. *J. Org. Chem.* 1992, 57, 2873; Boger, D. L.; McKie, J. A. *J. Org. Chem.* 1995, 60, 1271; Drost, K. J.; Cava, M. P. *J. Org. Chem.* 1991, 56, 2240; Aristoff, P. A.; Johnson, P. D. *J. Org. Chem.* 1992, 57, 6234; Mohamadi, F.; et al. *J. Med. Chem.* 1994, 37, 232; Ling, L.; et al. *Heterocyclic Commun.* 1997, 3, 405; Boger, D. L.; et al. *Synlett* 1997, 515; Boger, D. L.; et al. *Tetrahedron Lett.* 1998, 39, 2227; Kastrinsky, D. B.; Boger, D. L. *J. Org. Chem.* 2004, 69, 2284), 20 was prepared from 16 and converted to 21 enlisting a key 5-exo-trig aryl radical-alkene cyclization (Boger, D. L.; et al. *Tetrahedron Lett.* 1998, 39, 2227). See, Scheme 3, below, that also illustrates the synthesis of the analog of CBI-TMI, 9.

Compound 20 was converted to 21 enlisting a key 5-exo-trig aryl radical-alkene cyclization (Boger, D. L.; et al. *Tetrahedron Lett.* 1998, 39, 2227). The product 21, like 14 ($\alpha$=1.19), was chromatographically resolved on a semi-preparative ChiralCel OD column ($\alpha$=1.42) providing each enantiomer, and 21 was coupled with 5,6,7-trimethoxyindole-2-carboxylic acid (15) upon N-Boc deprotection to provide 9.

Stability and Reactivity of the N-Acyl O-Amino Phenol Derivatives

Clear from efforts directed at their preparation, the N-acyl amino phenol prodrugs displayed a useful range of stability, yet were susceptible to cleavage of the critical N—O bond. As might be anticipated, their relative stability followed the order of 4>5>6>7 with 4 and 5 withstanding even long term storage effectively, but with 7 noticeably deteriorating over time. Derivatives 4 and 6, as well as 7, proved surprisingly robust to acidic conditions (TFA-CH$_2$Cl$_2$, 4 NHCl-EtOAc), and stable to mild base treatment in nonpolar, aprotic solvents (Et$_3$N or DMAP, CH$_2$Cl$_2$), but exhibited a diminished stability as the solvent polarity increases: stable to NaHCO$_3$ in THF or THF-H$_2$O, but cleaved in NaHCO$_3$/DMF-H$_2$O or H$_2$O and DBU/CH$_3$CN. Similarly, 4 proved stable in MeOH, but 2 was released slowly upon treatment with NaHCO$_3$ or Na$_2$CO$_3$ in MeOH (2 hours, 23° C.). Most pertinent to the potential source of cleavage under physiological conditions, 4 was stable to treatment with BnSH in THF (2-72 hours, 23° C.) or MeOH (2-72 hours, 23° C.), and stable to treatment with BnSH in THF even in the presence of insoluble $NaHCO_3$ (2 hours, 23° C.), but is cleaved to release 2 upon treatment with BnSH in MeOH in the presence of $NaHCO_3$ (2 hours, 23° C.). Significantly, the stability of 4 was assessed in pH 7.0 phosphate buffer and within the limits of detection (HPLC, UV), no significant cleavage of the prodrug was observed over the time monitored (72 hours). The stability of 4 was monitored in human plasma (50 μg/100 μL, 10% DMSO) in which it displayed a half-life of 3 hours with release of the free drug 2.

Biological Properties

Cytotoxic Activity

The O-amino phenol derivatives bearing the N—O prodrug linkages and the various N-acyl substituents were assayed for cytotoxic activity alongside the parent drugs CBI-TMI (2) (Boger, D. L.; Yun, W. *J. Am. Chem. Soc.* 1994, 116, 7996) and mitomycin C (Boger, D. L.; et al. *Bioorg. Med. Chem. Lett.* 1991, 1, 115; Boger, D. L.; et al. *Bioorg. Med. Chem.* 1995, 3, 1429) as well as the two control standards 9 and 10 incapable of free phenol release. Three cell lines were examined including a standard L1210 cell line (mouse leukemia) as well as the mitomycin-sensitive (H460, expresses high levels of DT-Diaphorase) and resistant (H596, lacks DT-Diaphorase) non small cell lung cancer (NSCLC) cell lines, with results shown in the Table below.

Even more significantly, the relative potency of the prodrugs, when distinguishable, mirrors the expected ease of N—O bond cleavage (e.g. L1210: 7>6>5>4) suggesting fundamental chemical principles can be used to "tune" the reductive free drug release. Provocatively, the potency differences between the free drug 2 and the prodrugs diminish as the hypoxic character of the cell line increases; 4 is 10-fold less potent than 2 against L1210, but 2 and 4 are essentially equipotent against H460/H596.

More significantly and unlike mitomycin C, this reductive activation is not linked to the expression levels of DT-Diaphorase because 2 and 4-7 remain equipotent in the H460 or H596 cell lines, although H596 is 10-fold less sensitive than H460 to seco-CBI-TMI itself. This result illustrates that DT-Diaphorase is not mediating the reductive release of the drug from the O-amino phenol prodrugs, indicating that their utility is orthogonal to that of mitomycin. Rather, their behavior is consistent with the suggestion that the activation is nonenzymatic and likely is mediated in situ by appropriate nucleophiles.

Analogous trends are also observed with the CBI-TMI unnatural enantiomers albeit at concentrations that are approximately 100 to 1000-fold higher than that of the natural enantiomers as is seen in the Table below.

Natural enantiomer series

| Compd, R | IC$_{50}$ (nM) | | |
|---|---|---|---|
| | L1210 | H460 | H596 |
| mitomycin C | 40 | 20 | 5000 |
| 9, H | >100 | >100 | >100 |
| 10, OMe | 50 | >100 | >100 |
| 2, OH | 0.04 | 0.5 | 5 |
| 4, ONHBoc | 0.5 | 1 | 6 |
| 5, ONHAc | 0.3 | 0.7 | 7 |
| 6, ON(Ac)Boc | 0.2 | 0.6 | 5 |
| 7, ONPhth | 0.06 | 0.5 | 5 |

Several important trends emerged from these studies. First, the natural enantiomer control standards 9 and 10, incapable of free phenol release, were inactive against all three cell lines (IC$_{50}$>100 nM) being ≧10,000-fold less active than the free drug 2 (seco-CBI-TMI). In sharp contrast, the natural enantiomers of the O-amino phenol prodrugs exhibited potent cytotoxic activity approaching that of the free drug itself (1-0.1 times the activity of 2) indicating its successful release under the assay conditions.

Unnatural enantiomer series

| Compd, R | IC$_{50}$ (nM) | | |
|---|---|---|---|
| | L1210 | H460 | H596 |
| mitomycin C | 40 | 20 | 5000 |
| 9, H | 900 | 5500 | >10000 |
| 10, OMe | 800 | 5000 | >10000 |
| 2, OH | 5 | 50 | 300 |
| 4, ONHBoc | 160 | 900 | 6400 |
| 5, ONHAc | 100 | 700 | 6300 |
| 6, ON(Ac)Boc | 70 | 600 | 6300 |
| 7, ONPhth | 60 | 600 | 6000 |

Especially interesting and exciting was the behavior of the CBI-indole$_2$ prodrug. For this CBI analogue, only the NHBoc derivative was examined because it was the most stable of the N-acyl O-amino phenol prodrugs examined as is seen from the data below.

Natural enantiomer series

| | IC$_{50}$ (nM) | | |
|---|---|---|---|
| Compd, R | L1210 | H460 | H596 |
| mitomycin C | 40 | 20 | 5000 |
| 3, OH | 0.03 | 0.2 | 2 |
| 8, ONHBoc | 0.05 | 0.3 | 4 |

Unnatural enantiomer series

| | IC$_{50}$ (nM) | | |
|---|---|---|---|
| Compd, R | L1210 | H460 | H596 |
| mitomycin C | 40 | 20 | 5000 |
| 3, OH | 0.7 | 6 | 40 |
| 8, ONHBoc | 2 | 10 | 60 |

In each cell line examined, the prodrug 8 was essentially equipotent with CBI-indole$_2$ (3) itself, indicating effective release of the free drug under the conditions of the assay. In addition prodrug 8 proved to be exceptionally potent, being 100-1000 times more active than mitomycin C (IC$_{50}$=30-200 pM vs 20-40 nM) and it remained remarkably active against the mitomycin-resistant H596 cell line (IC$_{50}$=4 nM vs 5 μM). Even the unnatural enantiomer of prodrug 8, which was found to be 10-100 fold less active than the natural enantiomer, proved to be more active than mitomycin C. Given the efficacy of (+)-CBI-indole$_2$ in animal tumor models, (Boger, D. L.; Ishizaki, T.; Sakya, S. M.; Munk, S. A.; Kitos, P. A.; Jin, Q.; Besterman, J. M. Bioorg. Med. Chem. Lett. 1991, 1, 115; Boger, D. L.; Yun, W.; Han, N. Bioorg. Med. Chem. 1995, 3, 1429) it was especially interesting to compare 8 with 3 in vivo.

DNA Alkylation Selectivity and Efficiency

The DNA alkylation properties of 4 were examined alongside the parent drug CBI-TMI (2), and the two control standards 9 and 10 (incapable of spirocyclization) within w794 duplex DNA (Boger, D. L.; et al. Tetrahedron 1991, 47, 2661) for which results for an extensive series of duocarmycin analogues have been reported. The sites of DNA alkylation and its efficiency were directly assessed by thermally-induced singly 5' end-labeled duplex DNA strand cleavage following incubation with the agents (FIG. 8, natural enantiomers examined).

The reductively activated agent 4 was found to alkylate w794 DNA with an identical sequence selectivity as the parent agent CBI-TMI (2), albeit with a substantially reduced efficiency (1,000-10,000 fold). Similarly, the O-methyl ether 10 as well as 9 lacking a C4 substituent failed to exhibit significant observable DNA alkylation. In fact, 9 showed no appreciable DNA alkylation even under forcing conditions (37° C., 18 hours, data not shown), whereas the potentially more reactive O-methyl ether 10 (via assisted phenonium ion formation) displayed perhaps a trace amount of DNA alkylation (<0.01% that of 2) that could be attributed to either its direct, but much less facile, DNA alkylation or contaminant free phenol present in the synthetic sample of 10.

With detection of DNA alkylation by the prodrug 4 at the level observed (0.1-0.01% of 2), one cannot distinguish whether this is due to direct alkylation by 4 itself, trace release of 2 from 4 under the DNA incubation conditions (in situ N—O cleavage), or attributable to trace contaminate 2 in the synthetic samples of 4. What the results do indicate is that 4 is incapable of significant DNA alkylation in its own right (requires N—O bond cleavage), and that 4 is essentially stable to the DNA alkylation conditions examined requiring deliberate N—O bond cleavage to initiate effective DNA alkylation. These observations are consistent with the stability of 4 observed in pH 7.0 phosphate buffer. Significantly, the results then suggest that the in vitro cytotoxic activity of 4, and by analogy that of the related O-amino phenol prodrugs that all approach that of the parent drug CBI-TMI (2), is derived from in situ intracellular cleavage of the N—O bond and productive release of the active drug under the cell culture conditions.

In Vivo Antitumor Activity

The prodrug 8 was examined for in vivo efficacy alongside the parent drug 3 in a standard antitumor model enlisting L1210 murine leukemia implanted i.p. into DBA/2J mice. This model has been reported to respond well to the parent drugs of related compounds (Li, L. H.; et al. Invest. New Drugs 1991, 9, 137) and is a system that collaborators through the years have used to assess an extensive series of (+)-CBI-indole$_2$ analogues. Although not published, these latter studies provided the foundation on which examination of 8 is based.

With use the dose range (10-100 μg/kg) and the dosing schedule (administered three times i.p. on days 1, 5, and 9) found suitable for related parent drugs including (+)-CBI-indole$_2$ (3) (Boger, D. L.; et al. Bioorg. Med. Chem. Lett. 1991, 1, 115; Boger, D. L.; et al. Bioorg. Med. Chem. 1995, 3, 1429), the prodrug 8 was examined as is shown in the Table below.

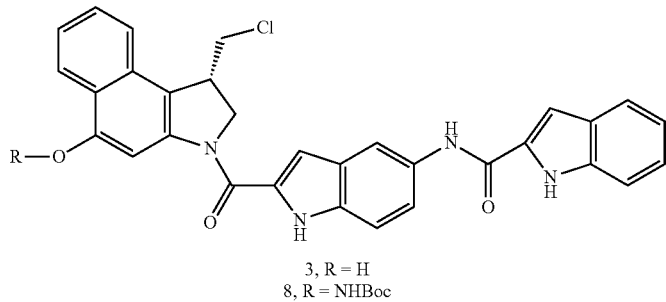

3, R = H
8, R = NHBoc

| Compound | Dose µg/kg | Mean Survival Period (MSP) (days) | Treated/Control (MSP × 100) | Surviving Mice |
|---|---|---|---|---|
| none | 0 | 20 | 100 | 0/6 |
| 8 | 10 | 25 | 120 | 0/6 |
| 8 | 30 | >145 | >730 | 2/6 |
| 8 | 100 | >310 | >1550 | 5/6 |
| 3 | 10 | 34 | 170 | 0/6 |
| 3 | 30 | >115 | >580 | 1/6 |
| 3 | 100 | 125 | 625 | 0/6 |

The dose at which a maximal response was observed for 8 corresponded closely to that of (+)-CBI-indole$_2$ (3) whereas its efficacy was significantly improved. This result indicates that the prodrug 8 (a) efficiently and effectively releases the free drug 3 in the in vivo model (reductive activation), and (b) that either the rate of release or the site of release enhances the efficacy of the drug. Moreover, the efficacy of 8 is extraordinary providing 5/6 long-term survivors at 52 weeks (365 days, T/C>1550) at the optimal dosing examined (100 µg/kg). Notably, little distinction between 3 and 8 was observed at days 30-100 except that the prodrug-treated animals appeared healthier, displaying little or no weight loss that was evident with 3 at the highest dosing.

With the prolonged management of the treated animals herein that exceeded the time frame typically allotted for such an in vivo antitumor assessment, it was observed that the surviving mice at day 90 treated with the free drug 3, but not the prodrug 8, eventually expired due to drug administration related complications. (This appears to arise from damage to the intraperitoneal cavity or its organs that originate with the bolus drug administration.) Although these administration effects would likely be capable of being managed with an optimized dosing schedule, this distinction between 3 and 8 in the long-term cures (>90 days) suggests the prodrug 8 offers significant advantages over the free drug administration.

It is also worth noting that these compounds are extraordinarily potent, requiring less than 1 mg of sample to conduct the entire in vivo antitumor testing, suggesting that clinical supplies of such agents could easily be supplied by chemical synthesis.

Confirming these observations, an analogous antitumor assessment was carried out independently at a second site utilizing a slightly different and harsher protocol for drug administration (neat DMSO vs 30% DMSO in 0.1% glucose). Although this assessment was terminated after 120 days, it similarly indicates that administration of the prodrug 8 is significantly less toxic than free drug 3, and that it is comparable or superior in terms of reducing deaths due to the disease, tumor counts, and tumor volume as seen from the Table below. Again, 7/10 long-term survivors were observed with prodrug 8 at day 120 at the optimal dosing (60 µg/kg).

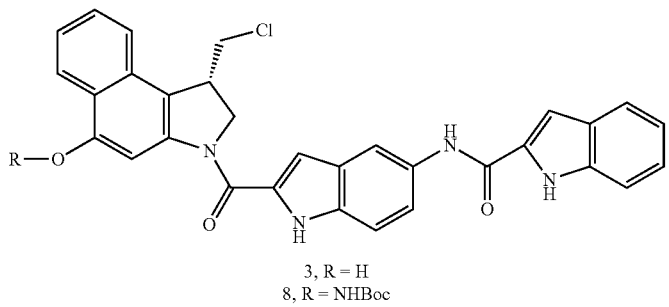

3, R = H
8, R = NHBoc

| Compound | Dose µg/kg | Mean Survival Period (MSP) (days) | Treated/Control (MSP × 100) | Surviving Mice |
|---|---|---|---|---|
| none | 0 | 22 | 100 | 0/10 |
| 8 | 10 | >46 | >210 | 2/10 |

| | | | | |
|---|---|---|---|---|
| | | -continued | | |
| 8 | 30 | >51 | >232 | 2/10 |
| 8 | 60 | >93 | >425 | 7/10 |
| 8 | 100 | >63 | >288 | 3/10 |
| 3 | 10 | >60 | >271 | 3/10 |
| 3 | 30 | >65 | >295 | 3/10 |
| 3 | 60 | >71 | >324 | 3/10 |
| 3 | 100 | 11 | 52 | 0/10 |

In the above Table, the second column is the dose in mg/kg of body weight of the animal that is administered i.p. (into the intraperitoneal cavity) on days 1, 5, and 9. The surviving mice are the number of mice that are still living after 120 days and the experiment was then terminated.

Experimental

DNA Alkylation Selectivity and Efficiency

The DNA alkylation reactions were performed by treatment of 4.5 μL of singly $^{32}$P 5'-end-labeled double-stranded w794 DNA (Boger, D. L.; et al. *Tetrahedron* 1991, 47, 2661) in TE buffer (10 mM Tris, 1 mM EDTA, pH 7.6) with 0.5 μL of agent in EtOH (at the specified concentration). The samples were incubated for 18 h at 4° C. Unbound agent was removed by EtOH precipitation of DNA (0.5 μL of 3.0 M sodium acetate and 12.5 μL of cold absolute EtOH) and the solutions were stored at −78° C. for 1 hour or longer. The DNA was pelleted by centrifugation at 4° C. (13000 rpm, 25 minutes), dried in a Savant Speed Vac concentrator, and resuspended in 5 μL of TE buffer (pH 7.6). Thermal depurination (3×10 minutes at 100° C.) was performed and then 2.5 μL of formamide dye solution was added to the cooled samples. Thermally denatured samples were assayed by gel electrophoresis [8% denaturing gel with 8 M urea in TBE buffer (89 mM Tris-borate, 2 mM EDTA)] followed by autoradiography of the dried gel using Kodak BIOMAX XAR film and a Picker Spectra™ intensifying screen.

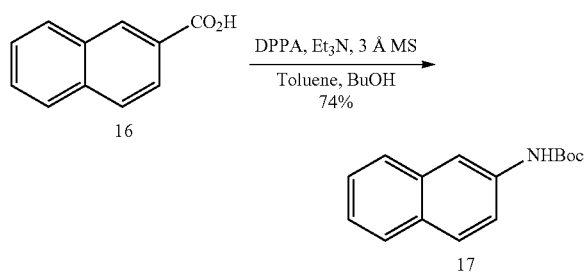

A solution of 2-naphthoic acid (16, 1.5 g, 8.7 mmol) in t-BuOH (50 mL) and toluene (50 mL) was treated with Et$_3$N (1.44 mL, 10 mmol), 3 Å molecular sieves (10 g) and diphenyl phosphorylazide (2.1 mL, 10 mmol). The reaction mixture was warmed at reflux for 24 h and then cooled to 23° C. The solid was filtered off through Celite and the solvent was removed in vacuo. The residue was dissolved in EtOAc (75 mL), and the organic phase was washed with 1 N aqueous HCl (50 mL×2), saturated aqueous NaHCO$_3$ (50 mL×2), dried over anhydrous sodium sulfate, and concentrated. Chromatography (SiO$_2$, 10% EtOAc/hexane) afforded 17 as a pale yellow solid (1.56 g, 74%): ESI-TOF HRMS m/z 266.1150 (M+Na$^+$, C$_{15}$H$_{17}$NO$_2$ requires 266.1151).

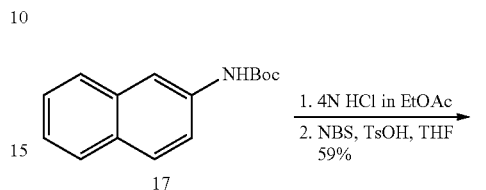

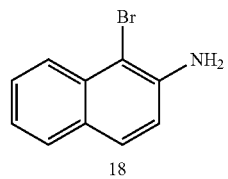

Compound 17 (1.5 g, 6.2 mmol) was treated with 4 N HCl-EtOAc (50 mL) for 1 hour before the solvent was removed to yield a white powder. The crude HCl salt (790 mg, 5.5 mmol), and TsOH (170 mg, 1.1 mmol) in THF (50 mL) cooled to 0° C. was treated with NBS (982 mg, 5.5 mmol) in THF (30 mL), and the solution was allowed to warm to 23° C. After stirring for 5 hours, the reaction mixture was washed with saturated aqueous NaHCO$_3$ (30 mL×2). The organic layer was dried over anhydrous sodium sulfate and was concentrated. Chromatography (SiO$_2$, 10% EtOAc/hexane) afforded 18 (863 mg, 59% for two steps): ESI-TOF HRMS m/z 221.9910 (M+H$^+$, C$_{10}$H$_8$BrN requires 221.9913).

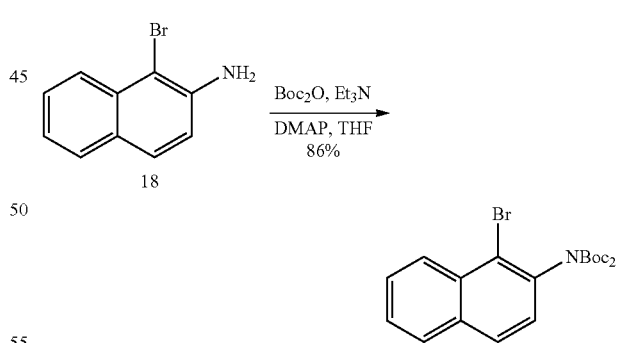

A solution of 18 (800 mg, 3.6 mmol) in CH$_2$Cl$_2$ was treated with Et$_3$N (496 μL, 3.6 mmol), DMAP (36 mg, 0.36 mmol), and Boc$_2$O (830 mg, 3.8 mmol) and the reaction mixture was stirred at 55° C. for 36 hours. The reaction mixture was cooled to 23° C. and washed with aqueous 1 N HCl (30 mL×2), and saturated aqueous NaHCO$_3$ (30 mL×2). The organic layer was dried over anhydrous sodium sulfate, and concentrated. Chromatography (SiO$_2$, 10% EtOAc/hexanes) provided the product as a white solid (1.25 g, 83%): ESI-TOF HRMS m/z 444.0780 (M+Na$^+$, C$_{20}$H$_{24}$BrNO$_4$ requires 444.0781).

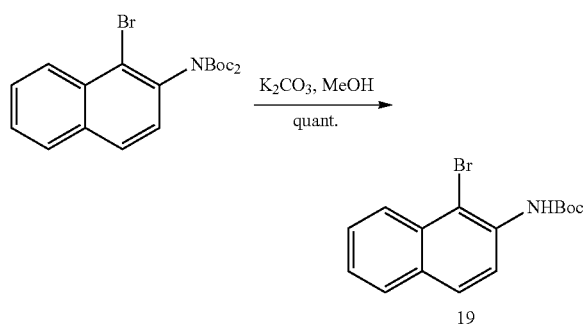

A solution of the product above (516 mg, 1.18 mmol) in MeOH (20 mL) was treated with K₂CO₃ (490 mg, 3.6 mmol), and the resulting mixture was warmed at reflux for 1.5 hours. The reaction mixture was allowed to cool to 23° C. and filtered through Celite to remove solid residue. The solvent was removed to yield 19 as a white solid (448 mg, quant.), which was sufficiently pure to use for next step without further purification: ESI-TOF HRMS m/z 344.0250 (M+Na⁺, $C_{15}H_{16}BrNO_2$ requires 344.0257).

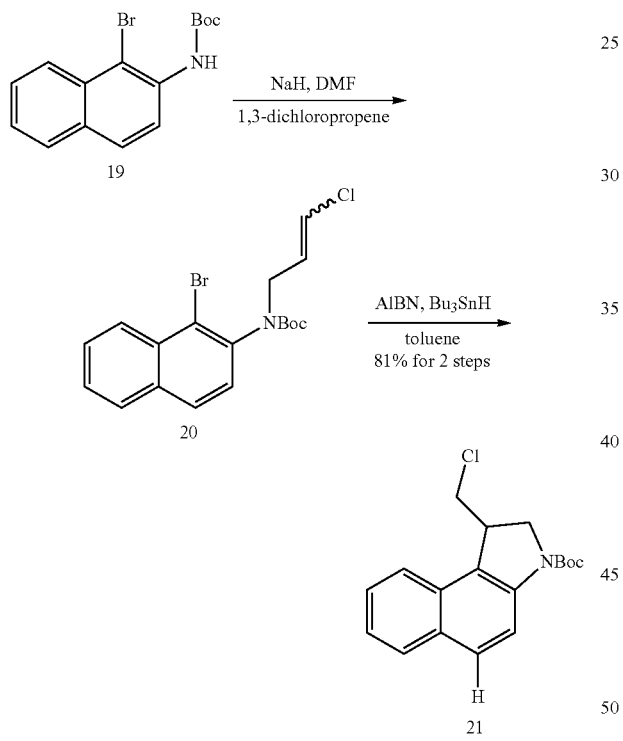

A solution of 19 (980 mg, 3 mmol) in DMF (20 mL) was treated with NaH (60%, 304 mg, 7.5 mmol) and Bu₄NI (11 mg, 0.3 mmol) at 0° C. After stirring for 15 minutes, 1,3-dichloropropene (0.8 mL, 9 mmol) was added, and the resulting mixture was warmed to 23° C. and stirred for another 4 hours. The reaction mixture was diluted with EtOAc (50 mL) and washed with saturated aqueous NH₄Cl (30 mL×2). The organic layer was dried over anhydrous sodium sulfate and concentrated. The crude product 20 was used for the next step without further purification.

A solution of crude 20 (1.0 g, 2.52 mmol) and AIBN (41 mg, 0.25 mmol) in degassed toluene (40 mL) was treated with Bu₃SnH (0.75 mL, 2.77 mmol). The resulting solution was purged with N₂ gas for 10 minutes and then warmed at reflux overnight (about 18 hours). The solvent was removed and the crude product was purified by chromatography (SiO₂, 10% EtOAc/hexanes) to yield racemic 21 as a white solid (780 mg, 97%). The two enantiomers were separated by chromatography (semiprep 2×25 cm Chiral OD column, 10% iPrOH/hexanes, flow rate=0.5 mL/min, $t_R$=35.5 min (natural), 25.0 min (unnatural), α=1.42): ESI-TOF HRMS m/z 340.1076 (M+H⁺, $C_{28}H_{20}ClNO_2$ requires 340.1075). 1S-21: $[α]^{23}_D$ −0.38 (c 0.18, CH₃OH), natural enantiomer; 1R-21: $[α]^{23}_D$ +0.46 (c 0.13, CH₃OH), unnatural enantiomer.

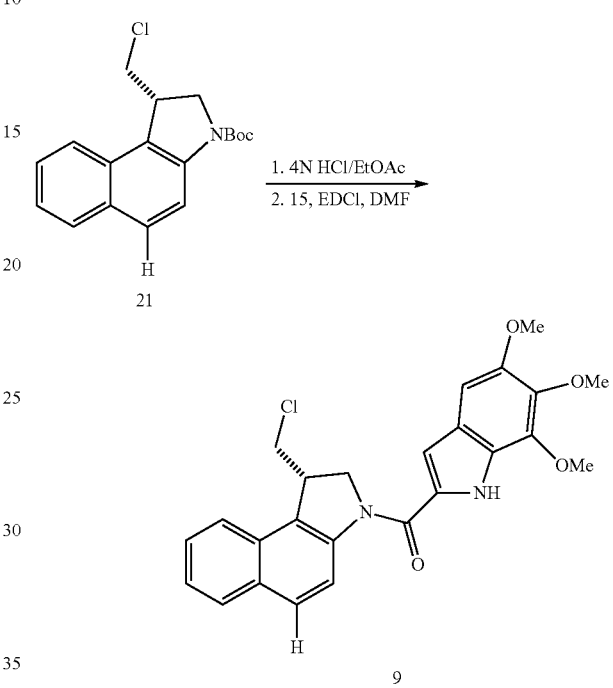

A sample of 21 (13 mg, 41 μmol) was treated with 4 NHCl-EtOAc (3 mL) for 30 min before the solvent was removed by a stream of N₂. The resulting crude HCl salt, 5,6,7-trimethoxyindol-2-carboxylic acid (15, 10.3 mg, 41 μmol) and EDCI (24 mg, 0.12 mmol) were dissolved in DMF (3 mL), and the resulting solution was stirred at 23° C. for 3 hours. The reaction mixture was diluted with EtOAc (15 mL) and washed with aqueous 1 N HCl (5 mL×2), and saturated aqueous NaHCO₃ (5 mL×2). The organic layer was dried over anhydrous sodium sulfate, and concentrated. PTLC (SiO₂, 50% EtOAc/hexanes) gave 9 as a white solid (13.6 mg, 74%): ESI-TOF HRMS m/z 451.1420 (M+H⁺, $C_{25}H_{23}ClN_2O_4$ requires 451.1419). 1S-9: $[α]^{23}_D$ −0.26 (c 0.46, THF), natural enantiomer; 1R-9: $[α]^{23}_D$ +0.27 (c 0.73, THF), unnatural enantiomer.

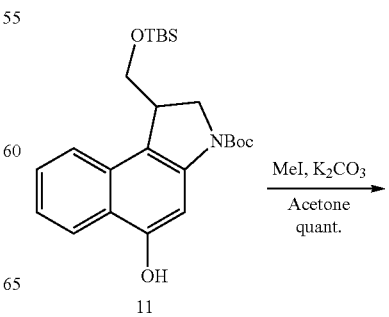

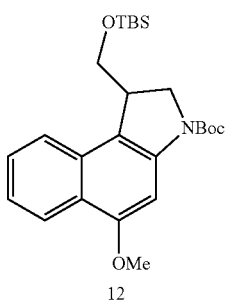

12

A solution of 11 (Kastrinsky, D. B.; Boger, D. L. *J. Org. Chem.* 2004, 69, 2284) (50 mg, 0.116 mmol), and methyl iodide (14.5 µL, 0.233 mmol) in acetone (12 mL) was treated with K$_2$CO$_3$ (48 mg, 0.349 mmol) at 23° C., and the resulting mixture was stirred at 23° C. for 3 hours. The reaction was diluted with water (10 mL) and extracted with EtOAc (15 mL×2). The combined organic layers were washed with water (15 mL×2), saturated aqueous NaCl (15 mL) and dried over anhydrous sodium sulfate. The solvent was removed and the crude product 12 was sufficiently pure for use without further purification (55 mg, quant.).

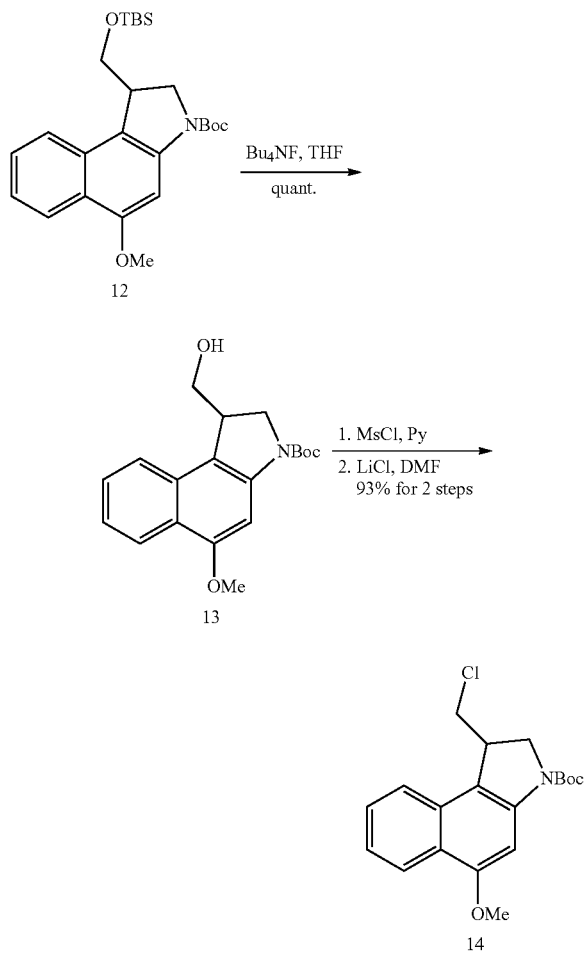 [SMILES: COc1cc2c(c3ccccc13)C(CO[Si](C)(C)C(C)(C)C)CN2C(=O)OC(C)(C)C ; COc1cc2c(c3ccccc13)C(CO)CN2C(=O)OC(C)(C)C ; COc1cc2c(c3ccccc13)C(CCl)CN2C(=O)OC(C)(C)C]

A solution of 12 (51 mg, 0.115 mmol) in THF (5 mL) was treated with Bu$_4$NF (1 M in THF, 575 µL, 0.575 mmol) at 23° C. After stirring at 23° C. for 1 hour, the reaction mixture was diluted with EtOAc (20 mL) and washed with water (10 mL), and saturated aqueous NaCl (10 mL). The organic layer was dried over anhydrous sodium sulfate and concentrated to afford pure 13 (40 mg, quant.). The above crude compound 13 (40 mg, 0.121 mmol) was dissolved in pyridine (2 mL). Methanesulfonyl chloride (59 µL, 0.607 mmol) was added at 0° C. After stirring at 23° C. for 6 hours, the reaction mixture was diluted with EtOAc (20 mL), and washed with water (10 mL×2), and saturated aqueous NaCl (10 mL). The organic layer was dried over anhydrous sodium sulfate and concentrated. The crude residue was dissolved in DMF (2 mL) and was treated with LiCl (26 mg, 0.607 mmol). After stirring at 23° C. for 3 days, the reaction mixture was diluted with EtOAc (20 mL) and washed with water (10 mL), saturated aqueous NaCl (10 mL). The organic layer was dried over anhydrous sodium sulfate and concentrated. Chromatography (SiO$_2$, 20% EtOAc/hexanes) afforded 14 (37.5 mg, 93% for two steps). The two enantiomers were separated by chromatography (semiprep 2×25 cm Chiral OD column, 10% iPrOH/hexanes, flow rate=0.5 mL/min, t$_R$=14.4 min (natural), 12.1 min (unnatural), α=1.19): 1S-14: [α]$^{23}$$_D$ –0.43 (c 0.28, THF), natural enantiomer; 1R-14: [α]$^{23}$$_D$ +0.45 (c 0.53, THF), unnatural enantiomer.

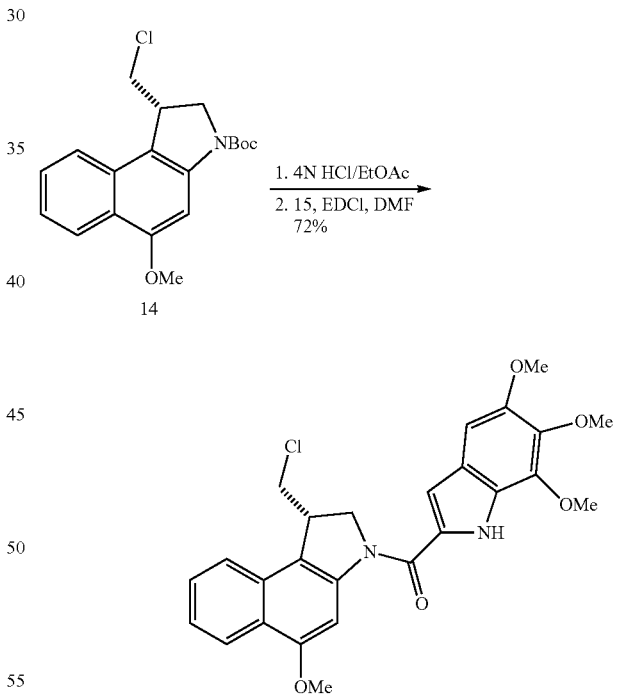

A sample of 14 (6.1 mg, 17 µmol) was treated with 4 NHCl-EtOAc (0.6 mL) for 30 minutes before the solvent was removed by a stream of N$_2$. The resulting crude HCl salt, 5,6,7-trimethoxyindol-2-carboxylic acid (15, 4.8 mg, 19 µmol) and EDCI (10.1 mg, 0.05 mmol) were dissolved in DMF (0.15 mL) and the resulting solution was stirred at 23° C. for 3 hours. EtOAc (10 mL) was added to the reaction mixture and the resulting solution was washed with aqueous 1 N HCl (5 mL×2), saturated aqueous NaHCO$_3$ (5 mL×2), dried over anhydrous sodium sulfate and concentrated. PTLC (SiO$_2$, 50% EtOAc/hexanes) gave 10 as a white solid (5.5 mg, 65%): ESI-TOF HRMS m/z 481.1521 (M+H$^+$, C$_{26}$H$_{25}$ClN$_2$O$_5$ requires 481.1525). 1S-10: [α]$^{23}_D$ −0.50 (c 0.31, THF), natural enantiomer; 1R-10: [α]$^{23}_D$ +0.86 (c 0.14, THF), unnatural enantiomer.

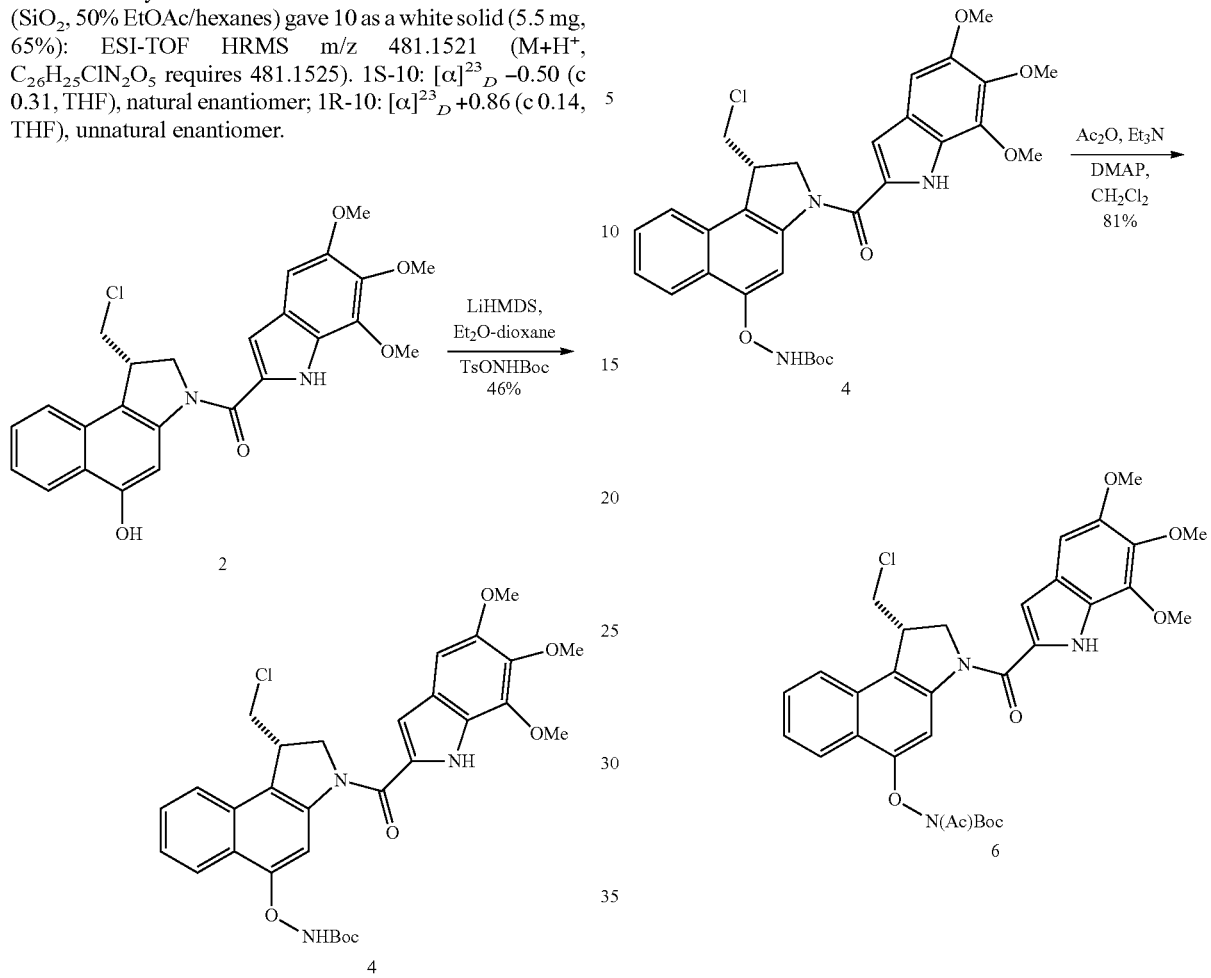

A solution of seco-CBI-TMI (Boger, D. L.; Yun, W. *J. Am. Chem. Soc.* 1994, 116, 7996) (2, 30 mg, 0.064 mmol) in ether-dioxane (1:1, 3 mL) was treated with LiHMDS (1 M in THF, 193 μL, 0.193 mmol) at 0° C., and the resulting mixture was stirred at 0° C. for 30 minutes. The resulting solution was treated with t-butyl-N-tosyloxycarbamate (55 mg, 0.193 mmol). The reaction mixture was allowed to warm to 23° C. and stirred for an additional 4 hours. The solution was diluted with EtOAc (20 mL) and washed with water (10 mL), and saturated aqueous NaCl (10 mL). The organic layer was dried over anhydrous sodium sulfate and concentrated. PTLC (SiO$_2$, 50% EtOAc/hexanes) afforded crude product (31.2 mg). To ensure the complete removal of any 2, the product (12 mg) was dissolved in THF (6 mL) and saturated aqueous NaHCO$_3$ (6 mL) was added. After stirring at 23° C. for 2 hours to promote spirocyclization of any residual 2 to the much more polar and easily separable CBI-TMI, the reaction mixture was diluted with EtOAc (20 mL), washed with water (10 mL) and saturated aqueous NaCl (10 mL). The organic layer was dried over anhydrous sodium sulfate and concentrated. PTLC (SiO$_2$, 20% EtOAc/hexanes) afforded 4 (6.6 mg, 46%) as a pale yellow solid: ESI-TOF HRMS m/z 582.2000 (M+H$^+$, C$_{30}$H$_{32}$ClN$_3$O$_7$ requires 582.2001). 1S-4: [α]$^{23}_D$ −0.39 (c 0.31, THF), natural enantiomer; 1R-4: [α]$^{23}_D$ +0.68 (c 0.44, THF), unnatural enantiomer.

A solution of 4 (3.4 mg, 0.00584 mmol) in CH$_2$Cl$_2$ (0.34 mL) was treated with acetic anhydride (2.7 μL, 0.0292 mmol), Et$_3$N (4.1 μL, 0.0292 mmol) and DMAP (cat). After the resulting mixture was stirred at 23° C. for 12 hours, the solvent was removed and the residue was purified by PTLC (SiO$_2$, 50% EtOAc/hexanes) to afford 6 (2.9 mg, 81%): ESI-TOF HRMS m/z 642.2102 (M+H$^+$, C$_{32}$H$_{34}$ClN$_3$O$_8$ requires 642.2107). 1S-6: [α]$^{23}_D$ −0.43 (c 0.23, THF), natural enantiomer; 1R-6: [α]$^{23}_D$ +0.54 (c 0.52, THF), unnatural enantiomer.

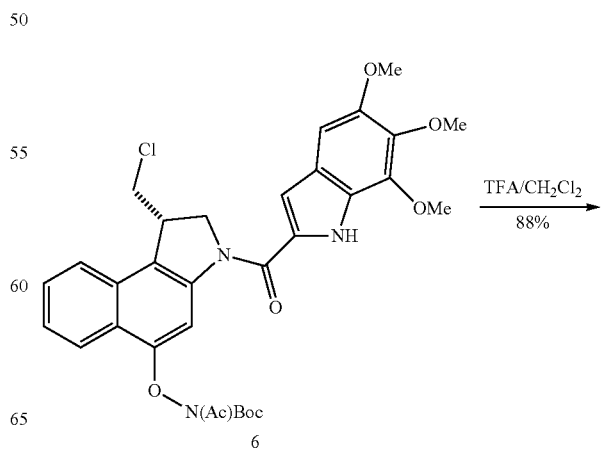

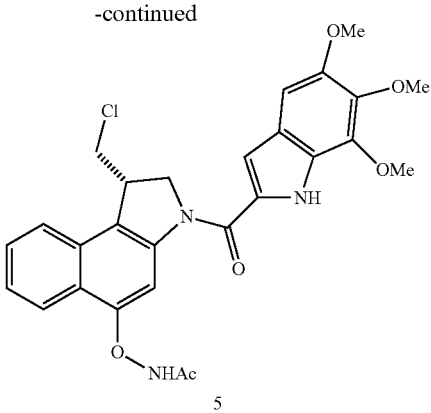

5

A solution of 6 (3.1 mg, 0.0053 mmol) in CH$_2$Cl$_2$ (1 mL) was treated with TFA (1 mL) at 23° C. for 3 hours. The solvent and excess TFA were removed and the residue was purified by PTLC (SiO$_2$, 50% EtOAc/hexanes) to afford 5 (2.3 mg, 88%): ESI-TOF HRMS m/z 522.1431 (M−H, C$_{22}$H$_{26}$ClN$_3$O$_6$ requires 522.1437). 1S-5: $[\alpha]^{23}_D$ −1.2 (c 0.10, THF), natural enantiomer; 1R-5: $[\alpha]^{23}_D$ +0.76 (c 0.21, THF), unnatural enantiomer.

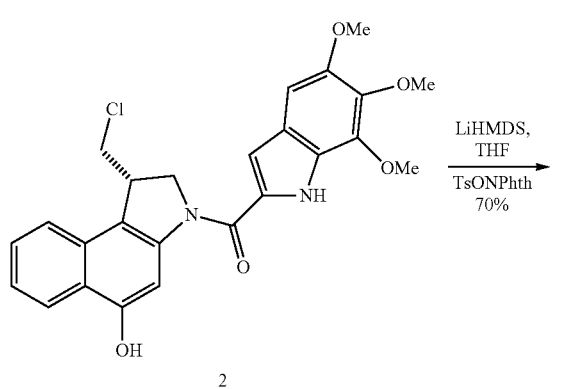

2

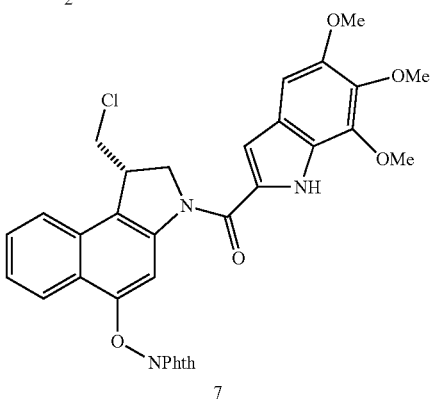

7

A solution of seco-CBI-TMI (2, 5.0 mg, 0.011 mmol) in THF (0.5 mL) was treated with LiHMDS (1 M in THF, 13 μL, 0.013 mmol) at −78° C., and the resulting mixture was stirred at −78° C. for 30 minutes. The resulting solution was treated with N-p-tolylsulfonyloxyphthalimide (5.1 mg, 0.016 mmol). The reaction mixture was stirred at 23° C. for an additional 60 minutes. The solution was diluted with EtOAc (10 mL) and washed with water (5 mL), and saturated aqueous NaCl (5 mL). The organic layer was dried over anhydrous sodium sulfate and concentrated. PTLC (SiO$_2$, 50% EtOAc/hexanes) afforded 7 (4.6 mg, 70%) as a pale yellow solid: 1S-7: $[\alpha]^{23}_D$ −0.42 (c 0.28, THF), natural enantiomer; 1R-7: $[\alpha]^{23}_D$ +0.53 (c 0.36, THF), unnatural enantiomer.

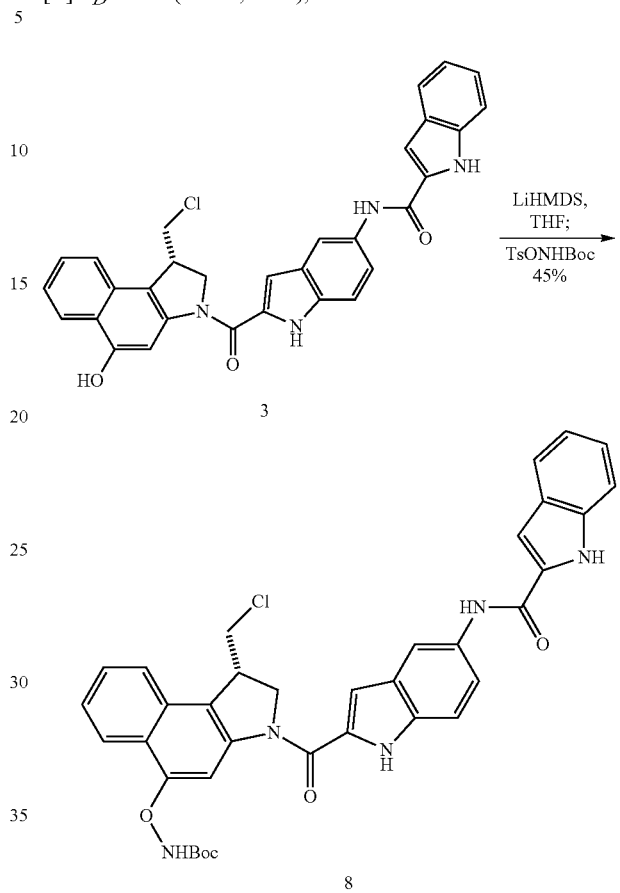

A solution of seco-CBI-indole$_2$ (Boger, D. L.; Yun, W.; Han, N. *Bioorg. Med. Chem.* 1995, 3, 1429) (3, 16.5 mg, 0.031 mmol) in THF (1.5 mL) was treated with LiHMDS (1 M in THF, 93 μL, 0.093 mmol) at 0° C. and the mixture was stirred at 0° C. for 30 minutes. The resulting solution was treated with t-butyl-N-tosyloxycarbamate (26.6 mg, 0.093 mmol), and the reaction mixture was allowed to warm to 23° C. and stirred for an additional 4 hours. The solution was diluted with EtOAc (20 mL) and washed with water (10 mL), and saturated aqueous NaCl (10 mL). The organic layer was dried over anhydrous sodium sulfate and concentrated. PTLC (SiO$_2$, 50% THF/hexanes) afforded 8 (12.0 mg). The product (12 mg) was dissolved in THF (6 mL) and treated with saturated aqueous NaHCO$_3$ (6 mL) to promote the spirocyclization of any residual 3. After stirring at 23° C. for 2 hours, the reaction mixture was diluted with EtOAc (20 mL), washed with water (10 mL) and saturated aqueous NaCl (10 mL). The organic layer was dried over anhydrous sodium sulfate and concentrated. PTLC (SiO$_2$, 20% THF/hexanes) afforded 8 (9.0 mg, 45%): ESI-TOF HRMS m/z 650.2150 (M+H$^+$, C$_{36}$H$_{32}$ClN$_5$O$_5$ requires 650.2165). 1S-8: $[\alpha]^{23}_D$ +2.1 (c 0.50, THF), natural enantiomer; 1R-8: $[\alpha]^{23}_D$ −2.0 (c 0.89, THF), unnatural enantiomer.

In Vivo Antitumor Activity

DBA/2J mice were purchased from Jackson Laboratory (Bar Harbor, Me.) and housed in the animal facility at The Scripps Research Institute. L1210 tumor cells, originally isolated from DBA/2 mice, were cultured in DMEM medium containing 5% fetal calf serum. For tumor implantation, DBA/2J mice were i.p. injected with $1\times10^5$ L1210 cells at day 0.

Compounds 3 and 8 were formulated with 30% DMSO plus 0.1% glucose solution. Treatment doses of drugs (0, 10, 30, 100 lg/kg wt. of animal) were i.p. injected consecutively on day 1, 5 and 9. The study was performed with six mice per group. Tumor growth in the peritoneal cavity was monitored daily and the death of animals was recorded. If necessary, weights of animals were measured once a week. To date this monitoring of the animals has lasted 365 days.

An analogous study with 10 mice per group was performed at the University of Kansas with the distinction that the compounds were administered in neat DMSO (0, 10, 30, 60, 100 lg/kg wt. of animal) and the study was terminated after 120 days.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed is:

1. An N-acyl O-amino CBI derivative represented by Formula I:

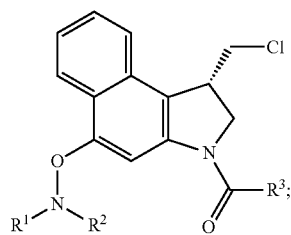

Formula I wherein:
  $R^1$ is selected from the group of radicals consisting of —C(O)(C$_1$-C$_6$ alkyl), —C(O)O(C$_1$-C$_{10}$ alkyl), —C(O)(C$_2$-C$_6$ alkenyl), —C(O)O(C$_2$-C$_6$ alkenyl), and —C(O)aryl;
  $R^2$ is selected from the group of radicals consisting of hydrogen, —C(O)(C$_1$-C$_6$ alkyl), —C(O)O(C$_1$-C$_{10}$ alkyl), —C(O)(C$_2$-C$_6$ alkenyl), and —C(O)O(C$_2$-C$_6$ alkenyl); or, alternatively,
  $R^1$ and $R^2$ are combined to form a cyclic structure selected from the group consisting of divalent radicals represented as follows:

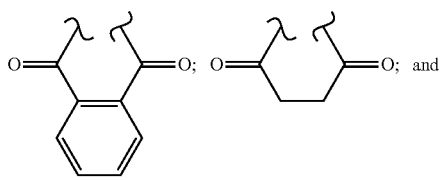

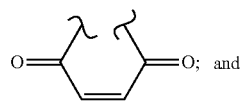

$R^3$ is selected from group consisting of radicals represented as follows:

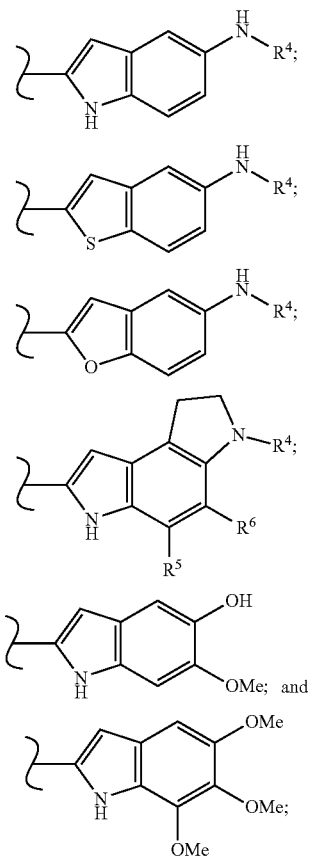

wherein:
  $R^4$ is selected from group consisting of radicals represented as follows:

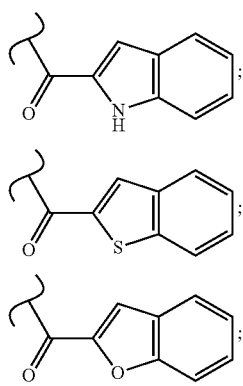

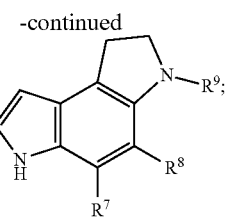

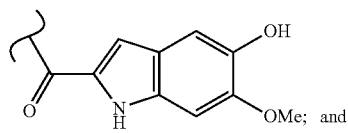

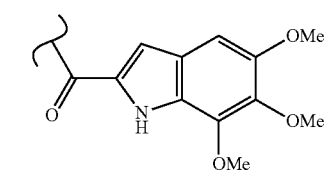

$R^5$, $R^6$, $R^7$ and $R^8$ are each independently selected from the group of radicals consisting of —H, —OH, —O($C_1$-$C_6$ alkyl), —($C_1$-$C_6$ alkyl) and halogen; and $R^9$ is selected from the group of radicals consisting of —H, —C(O)O($C_1$-$C_6$ alkyl), —C(O) ($C_1$-$C_6$ alkyl), —C(O)$NH_2$, —C(O)$NHNH_2$, and —C(O)NHNHC(O)O($C_1$-$C_6$ alkyl).

2. The N-acyl O-amino CBI derivative according to claim 1, wherein $R^1$ is selected from the group of radicals consisting of —C(O) ($C_1$-$C_6$ alkyl) and —C(O)O($C_1$-$C_{10}$ alkyl); $R^2$ is selected from the group of radicals consisting of hydrogen, —C(O)($C_1$-$C_6$ alkyl), and —C(O)O($C_1$-$C_{10}$ alkyl); or, alternatively, $R^1$ and $R^2$ can combine to form a cyclic divalent radical represented by the following structure:

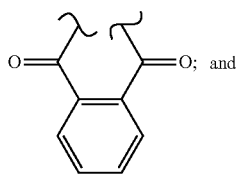

$R^3$ is selected from the group consisting of the following radicals:

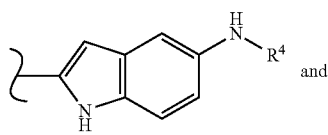

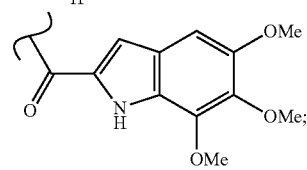

wherein:
$R^4$ is represented by the following structure:

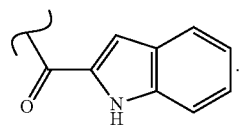

3. The N-acyl O-amino CBI derivative according to claim 2 represented by the following structure:

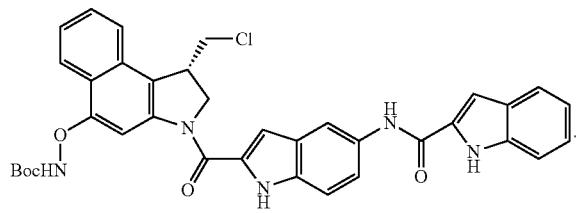 [SMILES: CC(C)(C)OC(=O)NOc1cc2c(c3ccccc13)[C@H](CCl)CN2C(=O)c1cc2cc(NC(=O)c3cc4ccccc4[nH]3)ccc2[nH]1]

4. The N-acyl O-amino CBI derivative according to claim 2 represented by the following structure:

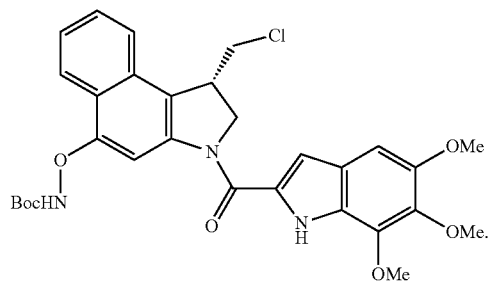 [SMILES: COc1cc2cc(C(=O)N3C[C@@H](CCl)c4c3cc(ONC(=O)OC(C)(C)C)c3ccccc43)[nH]c2c(OC)c1OC]

5. The N-acyl O-amino CBI derivative according to claim 2 represented by the following structure:

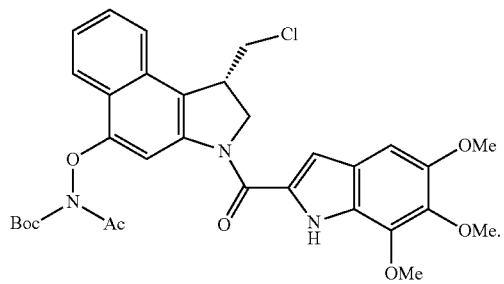 [SMILES: COc1cc2cc(C(=O)N3C[C@@H](CCl)c4c3cc(ON(C(C)=O)C(=O)OC(C)(C)C)c3ccccc43)[nH]c2c(OC)c1OC]

6. The N-acyl O-amino CBI derivative according to claim 2 represented by the following structure:

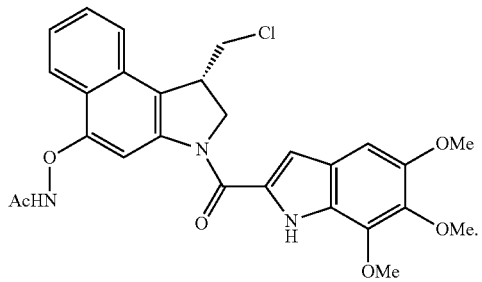 [SMILES: COc1cc2cc(C(=O)N3C[C@@H](CCl)c4c3cc(ONC(C)=O)c3ccccc43)[nH]c2c(OC)c1OC]

7. The N-acyl O-amino CBI derivative according to claim 2 represented by the following structure:

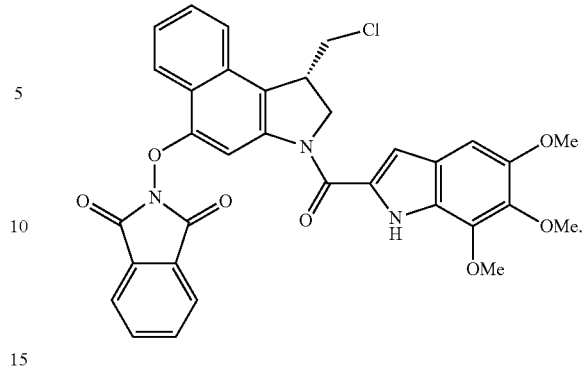

8. A process for treating a proliferative disease in a mammal, wherein said proliferative disease is leukemia, comprising the step of administering an effective amount of a compound of claim 1.

* * * * *